US012651653B2

(12) United States Patent
Torben-Nielsen et al.

(10) Patent No.: US 12,651,653 B2
(45) Date of Patent: Jun. 9, 2026

(54) MACHINE LEARNING BASED MEDICAL DATA CHECKER

(71) Applicant: Roche Molecular Systems, Inc., Pleasanton, CA (US)

(72) Inventors: Benjamin Torben-Nielsen, Basel (CH); Fernando Garcia-Alcalde, Basel (CH); Vincent Mauduit, Basel (CH); Corentin Christophe Karim Guerendel, Basel (CH); Phil Pascal Arnold, Basel (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 283 days.

(21) Appl. No.: 18/065,171

(22) Filed: Dec. 13, 2022

(65) Prior Publication Data

US 2023/0112591 A1     Apr. 13, 2023

Related U.S. Application Data

(63) Continuation of application No. PCT/US2021/038925, filed on Jun. 24, 2021.
(Continued)

(51) Int. Cl.
*G16H 10/60* (2018.01)
*G06T 7/00* (2017.01)
(Continued)

(52) U.S. Cl.
CPC .......... *G16H 10/60* (2018.01); *G06T 7/0012* (2013.01); *G16H 30/20* (2018.01); *G16H 50/20* (2018.01);
(Continued)

(58) Field of Classification Search
CPC ........ G16H 10/60; G16H 30/20; G16H 50/20; G06T 7/0012; G06T 2207/20081; G06T 2207/30096
See application file for complete search history.

(56) References Cited

U.S. PATENT DOCUMENTS

| | | | | |
|---|---|---|---|---|
| 9,785,754 | B2 * | 10/2017 | Pedrazzini | ............. G16H 10/40 |
| 11,189,367 | B2 * | 11/2021 | Lisowska | ............... G06N 20/00 |
| 2024/0037747 | A1 * | 2/2024 | Raedt | ................... G06V 20/698 |

FOREIGN PATENT DOCUMENTS

| | | | |
|---|---|---|---|
| JP | 2017167965 A | 9/2017 | |
| WO | 2019/183596 A1 | 9/2019 | |
| WO | WO-2021099584 A1 * | 5/2021 | ........... G06F 18/214 |

OTHER PUBLICATIONS

Chen, Cheng, et al. "Unsupervised bidirectional cross-modality adaptation via deeply synergistic image and feature alignment for medical image segmentation." IEEE transactions on medical imaging 39.7 (2020): 2494-2505.*
(Continued)

*Primary Examiner* — Shefali D Goradia
(74) *Attorney, Agent, or Firm* — Kilpatrick Townsend and Stockton LLP

(57)     ABSTRACT

A method of verifying multi-modal medical data is proposed. The method comprises: accessing multi-modal medical data of a subject, the multi-modal medical data comprising a medical image of a specimen slide, wherein a specimen in the specimen slide was collected from the subject; generating a prediction pertaining to a biological attribute of the medical image based on the medical image; determining a degree of consistency between the biological attribute of the medical image and other modalities of the multi-modal medical data; and outputting, based on the degree of consistency, an indication of whether the multi-modal medical data contain inconsistency.

20 Claims, 27 Drawing Sheets

Related U.S. Application Data

(60) Provisional application No. 63/043,691, filed on Jun. 24, 2020.

(51) Int. Cl.
G16H 30/20 (2018.01)
G16H 50/20 (2018.01)

(52) U.S. Cl.
CPC ............... *G06T 2207/20081* (2013.01); *G06T 2207/30096* (2013.01)

(56) References Cited

OTHER PUBLICATIONS

Kawauchi, Keisuke et al., A convolutional neural network-based system to prevent patient misidentification in FDG-PET examinations, Nature.com/Scientific Reports, 2019, 9 pp., vol. 9, Article 7192.

Office Action in Japanese Appln. 2022-580275 mailed Jul. 8, 2025; 4 pages.

International Search Report and Written Opinion in PCT/US2021/038925 mailed Jan. 12, 2022; 20 pages.

Astion, Right Patient, Wrong Sample. PSNet [internet], Dec. 1, 2006; 8 pages; Rockville (MD): Agency for Healthcare Research and Quality, US Department of Health and Human Services.

Pfeifer, Liu, Rate of Occult Specimen Provenance Complications in Routine Clinical Practice, *American Journal of Clinical Pathology*, vol. 139, Issue 1, Jan. 2013, pp. 93-100.

Lerner, Bush, Kenler, Dorfman, Morgan, Boyd, Burak, Fine; Abstract P5-02-08: Incidence of misattributed specimen provenance among surgical breast biopsies. *Cancer Res* May 1, 2015; 75 (9_Supplement): P5-02-08.

Boja, Emily, Živana Težak, Bing Zhang, Pei Wang, Elaine Johanson, Denise Hinton, and Henry Rodriguez. "Right data for right patient—A precisionFDA NCI-CPTAC multi-omics mislabeling challenge." *Nature medicine* 24, No. 9 (2018): 1301-1302.

Wojno, Kirk, John Hornberger, Paul Schellhammer, Minghan Dai, and Travis Morgan. "The clinical and economic implications of specimen provenance complications in diagnostic prostate biopsies." *The Journal of Urology* 193, No. 4 (2015): 1170-1177.

Rosenbaum, Matthew W., and Jason M. Baron. "Using machine learning-based multianalyte delta checks to detect wrong blood in tube errors." *American Journal of Clinical Pathology* 150, No. 6 (2018): 555-566.

* cited by examiner

100

340 →

| Count of tiles classified as part of a breast | Count of tiles classified as part of a lung |
|---|---|
| 20 | 100 |

350 →

| Scaled count of tiles classified as part of a breast | Scaled count of tiles classified as part of a lung |
|---|---|
| 19 | 10 |

Figure 8B:
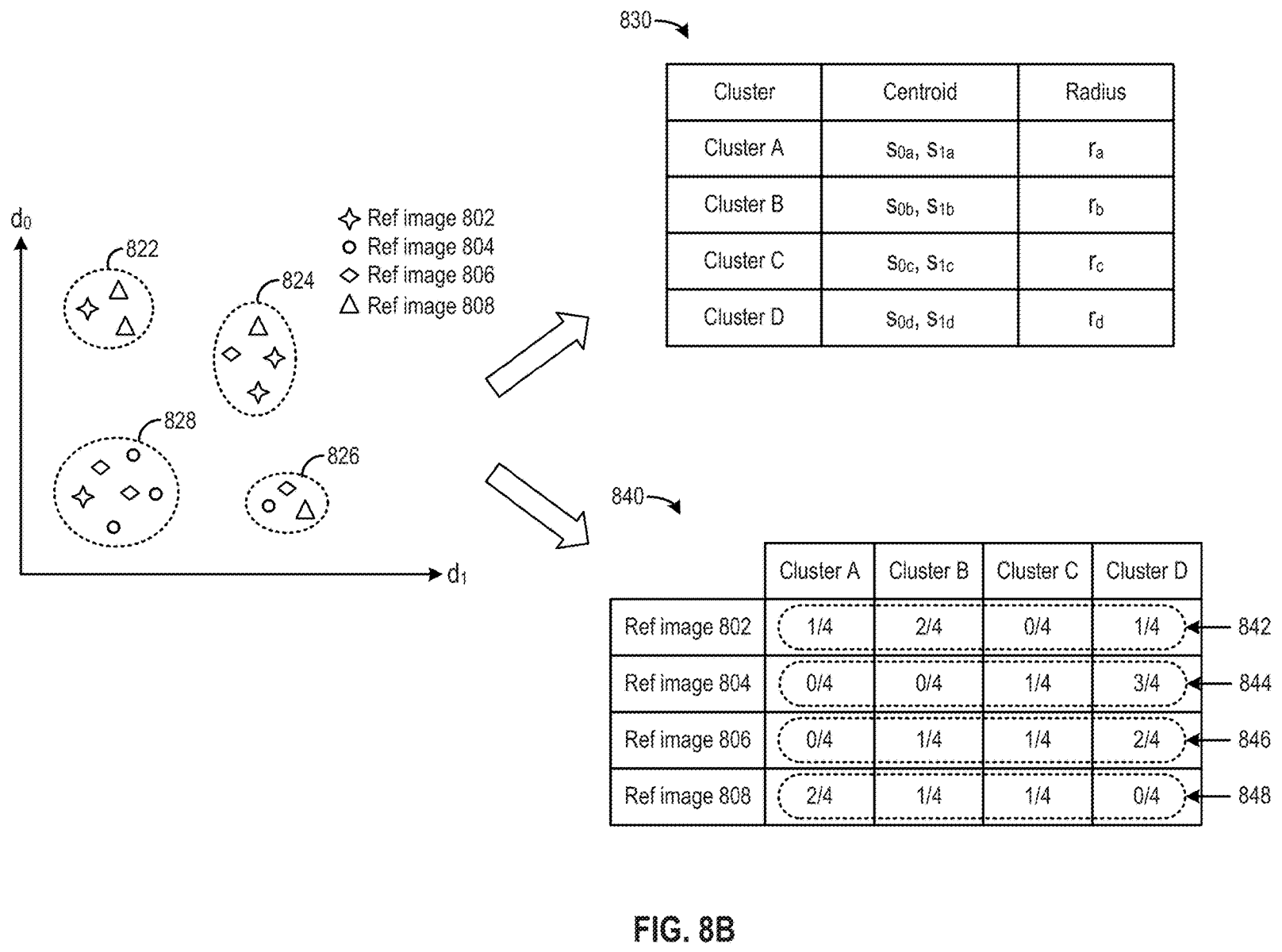

| Cluster | Centroid | Radius |
|---|---|---|
| Cluster A | $S_{0a}, S_{1a}$ | $r_a$ |
| Cluster B | $S_{0b}, S_{1b}$ | $r_b$ |
| Cluster C | $S_{0c}, S_{1c}$ | $r_c$ |
| Cluster D | $S_{0d}, S_{1d}$ | $r_d$ |

840

| | Cluster A | Cluster B | Cluster C | Cluster D | |
|---|---|---|---|---|---|
| Ref image 802 | 1/4 | 2/4 | 0/4 | 1/4 | 842 |
| Ref image 804 | 0/4 | 0/4 | 1/4 | 3/4 | 844 |
| Ref image 806 | 0/4 | 1/4 | 1/4 | 2/4 | 846 |
| Ref image 808 | 2/4 | 1/4 | 1/4 | 0/4 | 848 |

◇ Ref image 802
o Ref image 804
◇ Ref image 806
△ Ref image 808

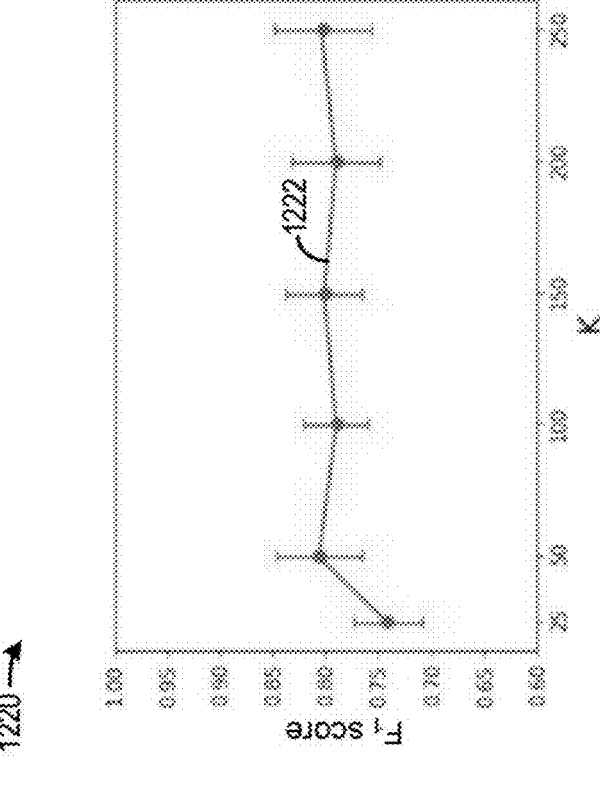
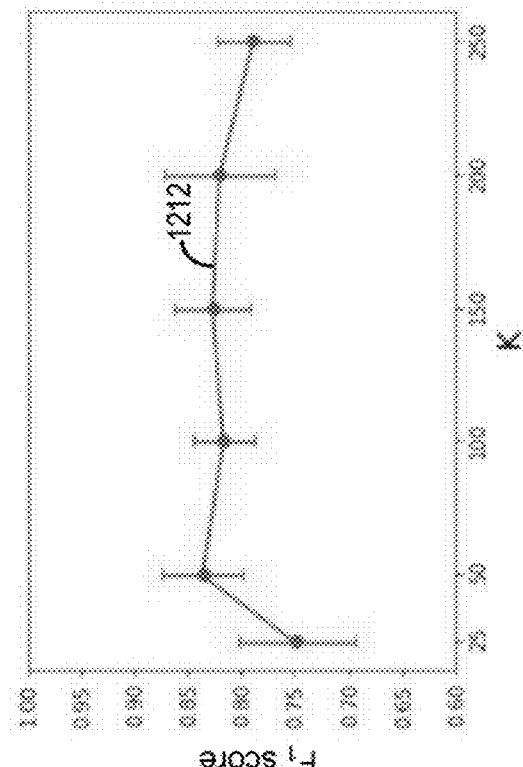
FIG. 12B

1300 ⟶

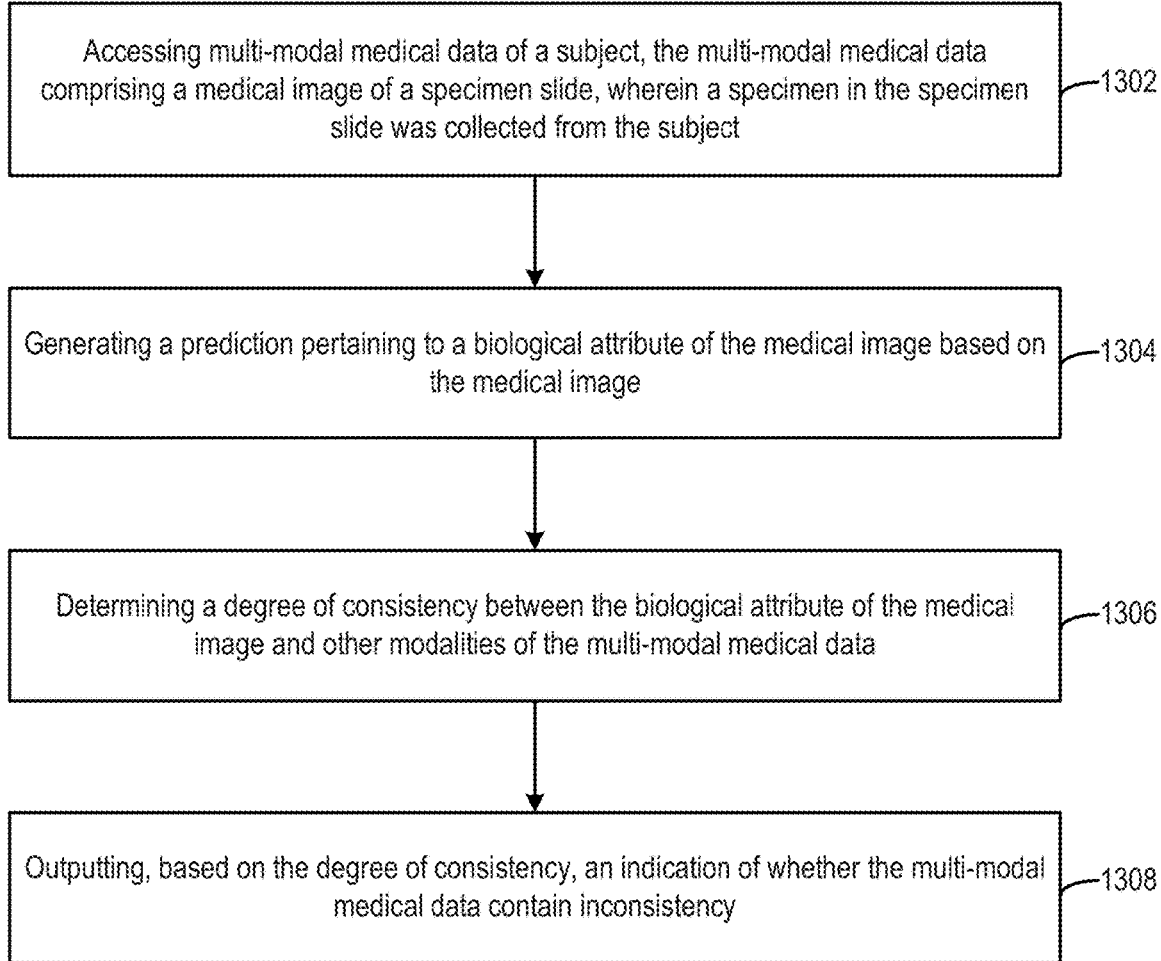

Accessing multi-modal medical data of a subject, the multi-modal medical data comprising a medical image of a specimen slide, wherein a specimen in the specimen slide was collected from the subject ⎯1302

Generating a prediction pertaining to a biological attribute of the medical image based on the medical image ⎯1304

Determining a degree of consistency between the biological attribute of the medical image and other modalities of the multi-modal medical data ⎯1306

Outputting, based on the degree of consistency, an indication of whether the multi-modal medical data contain inconsistency ⎯1308

Inputting each tile of a plurality of tiles of the input medical image into a machine learning model to generate, for each tile, a tile-level prediction of the attribute ‑1312

Generating a slide-level prediction of the attribute for the input medical image based on aggregating the tile-level predictions of the plurality of tiles ‑1314

1400 ⟶

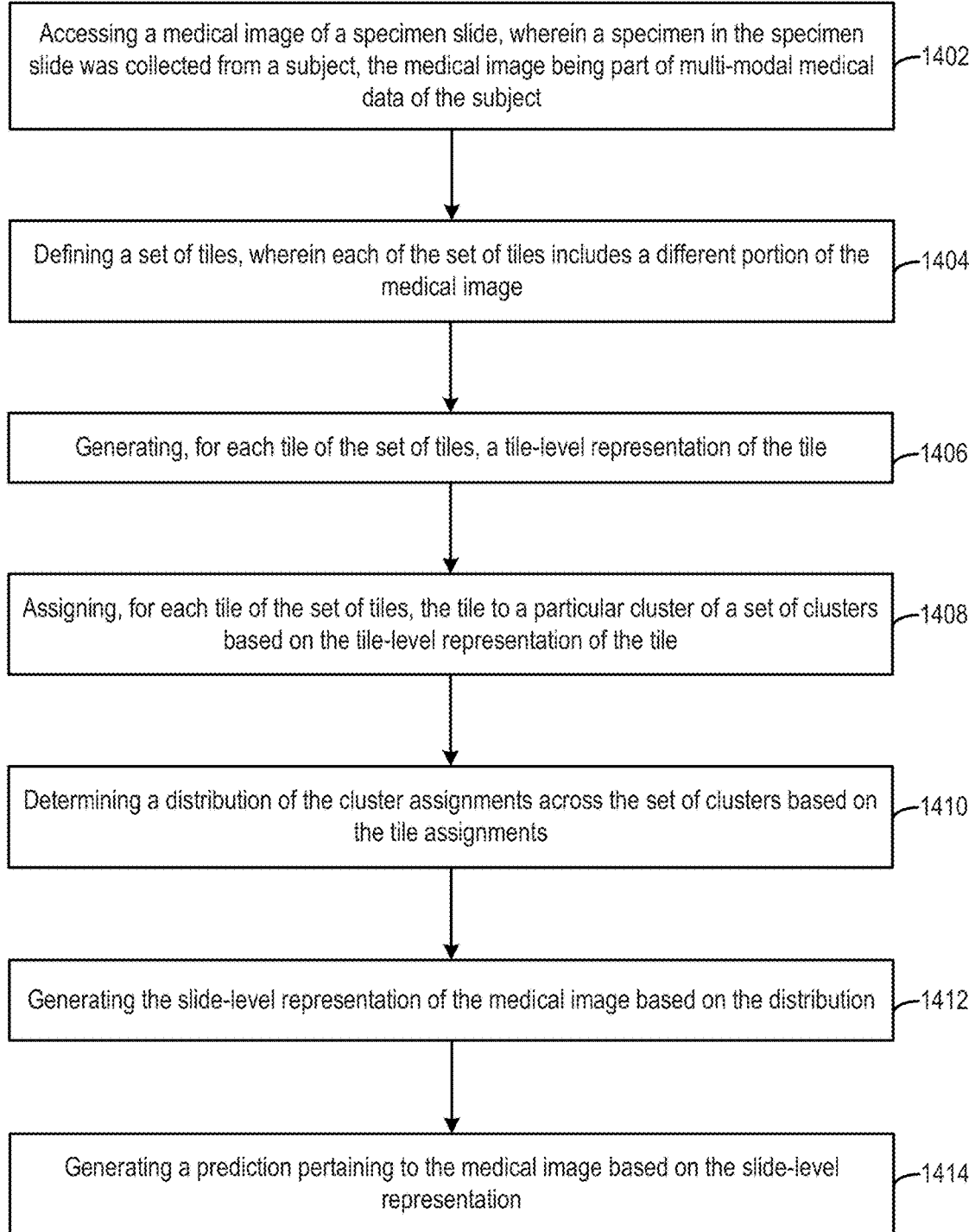

Accessing a medical image of a specimen slide, wherein a specimen in the specimen slide was collected from a subject, the medical image being part of multi-modal medical data of the subject — 1402

Defining a set of tiles, wherein each of the set of tiles includes a different portion of the medical image — 1404

Generating, for each tile of the set of tiles, a tile-level representation of the tile — 1406

Assigning, for each tile of the set of tiles, the tile to a particular cluster of a set of clusters based on the tile-level representation of the tile — 1408

Determining a distribution of the cluster assignments across the set of clusters based on the tile assignments — 1410

Generating the slide-level representation of the medical image based on the distribution — 1412

Generating a prediction pertaining to the medical image based on the slide-level representation — 1414

FIG. 14

MACHINE LEARNING BASED MEDICAL DATA CHECKER

CROSS-REFERENCE TO RELATED APPLICATIONS

The present application is a continuation of International Patent Application No. PCT/US2021/038925, filed Jun. 24, 2021, which claims the benefit of priority to U.S. Provisional Patent Application No. 63/043,691, filed Jun. 24, 2020, the disclosures of which are incorporated by reference for all purposes.

BACKGROUND

Every day, health care providers create a tremendous amount of medical data for different subjects (e.g., patients). The medical data for each subject can include multi-modal medical data. For example, for a cancer patient, multi-modal medical data can include biographic data of the subject, medical images of tissue specimens of the subject, analytic information of the tissue specimens, mutation status of the subject, etc. The multi-modal medical data can be stored in one or more databases. A clinician can obtain the multi-modal medical data for a subject from the databases perform a diagnosis based on the medical data and determine a treatment plan as well as a prognosis of the treatment for the subject. For example, based on a tumor size, the clinician can determine a stage of cancer the subject is in and decide the form of treatment (e.g., chemotherapy, radiation, or surgery) the subject should receive to prolong the survival of the subject. In addition, a clinician may consider the mutation status of the subject in determining a treatment. For example, some subjects carrying mutations in certain genes may be more responsive to certain types of therapies than subjects who do not carry those mutations, which can help the clinician decide the therapies for a subject.

The multi-modal medical data are typically assembled from multiple data sources and prepared by different health care providers. For example, the medical images can be prepared by a medical imaging department, whereas the biographic data can be prepared by an in-take department. Such arrangements can be prone to error. For example, identification errors can be introduced to the multi-modal medical data, where some or all of the medical data of a particular patient is swapped with those of another patient. One example of identification error is specimen provenance complication (also known as misattribution), in which a piece of data of one patient has been swapped with another patient. Identification errors can occur at any stage in a medical process—in the pre-analytic stage, in the analytic stage, and in the post-analytic stage. For example, an identification error can occur when a tissue specimen of a patient (or its image) has been swapped with another patient.

Undetected identification errors can seriously compromise clinical care if a clinical decision (e.g., a diagnostic decision or a treatment decision) made for a patient is based on medical data of another patient. Therefore, there is a need for an effective way of verifying or checking a large volume of medical data to detect and flag identification errors.

BRIEF SUMMARY

Disclosed herein are techniques for automated verification of multi-modal medical data of a subject (e.g., a patient). The multi-modal medical data can be verified, using the disclosed techniques, prior to being provided to a medical application. For example, the multi-modal medical data can be those of the subject and can include an input medical image of a specimen slide, which can be prepared from a tissue specimen removed from the subject. The multi-modal medical data can also include other modalities of medical data, such as analytics data of the tissue specimen. The analytics data may include, for example, a site/location of the tumor, a type of the tissue specimen (e.g., biopsy or resection), and a mutation status of the subject. The multi-modal medical data can also include biography data of the subject. The multi-modal medical data of the subject can be verified prior to the medical data being accessible on a medical application, to ensure that a user of the medical application (e.g., a clinician) is provided with multi-modal medical data that are verified to be consistent among the different modalities.

In some examples, the techniques include predicting, using one or more machine learning models and based on the input medical image of the multi-modal medical data, a biological attribute of the input medical image. The biological attribute may be associated with a type, and for each biological attribute type, there can be a range of biological attributes from which a biological attribute can be predicted for the input medical image. For example, the types of biological attributes can include a type of organ from which the tissue is extracted, and a range of biological attributes for the organ type can include, for example, brain, breast, bronchus and lung, or kidney. The types of biological attributes can also include a type of extraction method of the tissue specimen being observed in the image, and a range of biological attributes for extraction method type can include, for example, biopsy, or resection. Further, the types of biological attribute can also include a type of protein expression, and a range of biological attributes for a protein expression type can include, for example, a epidermal growth factor receptor (EGFR) protein, a KRAS protein, or tumor protein p53. The types of biological attributes can also include other information, such as a type of tumor cell in the specimen.

Moreover, the input medical image may include a set of tiles, each tile including a block of pixels. In some examples, a slide-level prediction of the biological attribute can be made for the input medical image based on performing tile-level predictions for each tile using one or more machine learning models, followed by aggregating the tile-level predictions. In some examples, the slide-level prediction can also be made based on inputting a slide-level representation of the input medical image to one or more machine learning models. In some examples, the slide-level representation can generated based on, for example, generating tile-level representations of the tiles, and assigning the tiles of the input medical image to clusters of reference tiles of reference medical images based on comparing the tile-level representations to reference tile-level representations of the clusters of reference tiles. The tile-level representations can be generated as embedding vectors.

The techniques further include determining consistencies between the predicted biological attribute of the input medical image and other modalities of the medical data and outputting an indication of whether the multi-modal medical data includes potential consistencies that can indicate misidentification error caused by, for example, an incorrect name listed in the biographic data, the tissue specimen being swapped with another subject, or the analytics data being swapped with another subject. The indication can be outputted in the medical application to warn a user of the medical application that the multi-modal medical data contain potential inconsistencies, and further investigation may be needed before the user can make a clinical decision based on that multi-modal medical data. In some examples, the slide-level representation of the input medical image can be used to perform a similarity search for similar medical images and other medical data of the subjects (e.g., diagnosis, treatment history, etc.) associated with the medical images, to facilitate a clinical decision for the subject of the input medical image.

These and other examples of the present disclosure are described in detail below. For example, other embodiments are directed to systems, devices, and computer-readable media associated with methods described herein.

A better understanding of the nature and advantages of the disclosed techniques may be gained with reference to the following detailed description and the accompanying drawings.

BRIEF DESCRIPTION OF THE DRAWINGS

The detailed description is set forth with reference to the accompanying figures.

FIG. 3A, FIG. 3B, and FIG. 3C illustrate example operations of medical data checker system of FIG. 2A and FIG. 2B, according to certain aspects of the present disclosure.

FIG. 8A, FIG. 8B, and FIG. 8C illustrate example components of medical data checker system of FIG. 2A and FIG. 2B and their operations, according to certain aspects of this disclosure.

FIG. 12A and FIG. 12B illustrate examples of a similarity search system and its operation, according to certain aspects of this disclosure.

FIG. 13A and FIG. 13B illustrate a method of performing a prediction of a diagnosis, according to certain aspects of this disclosure.

FIG. 14 illustrates a method of performing a prediction of a biological attribute of an medical image, according to certain aspects of this disclosure.

DETAILED DESCRIPTION

Figure 1A:
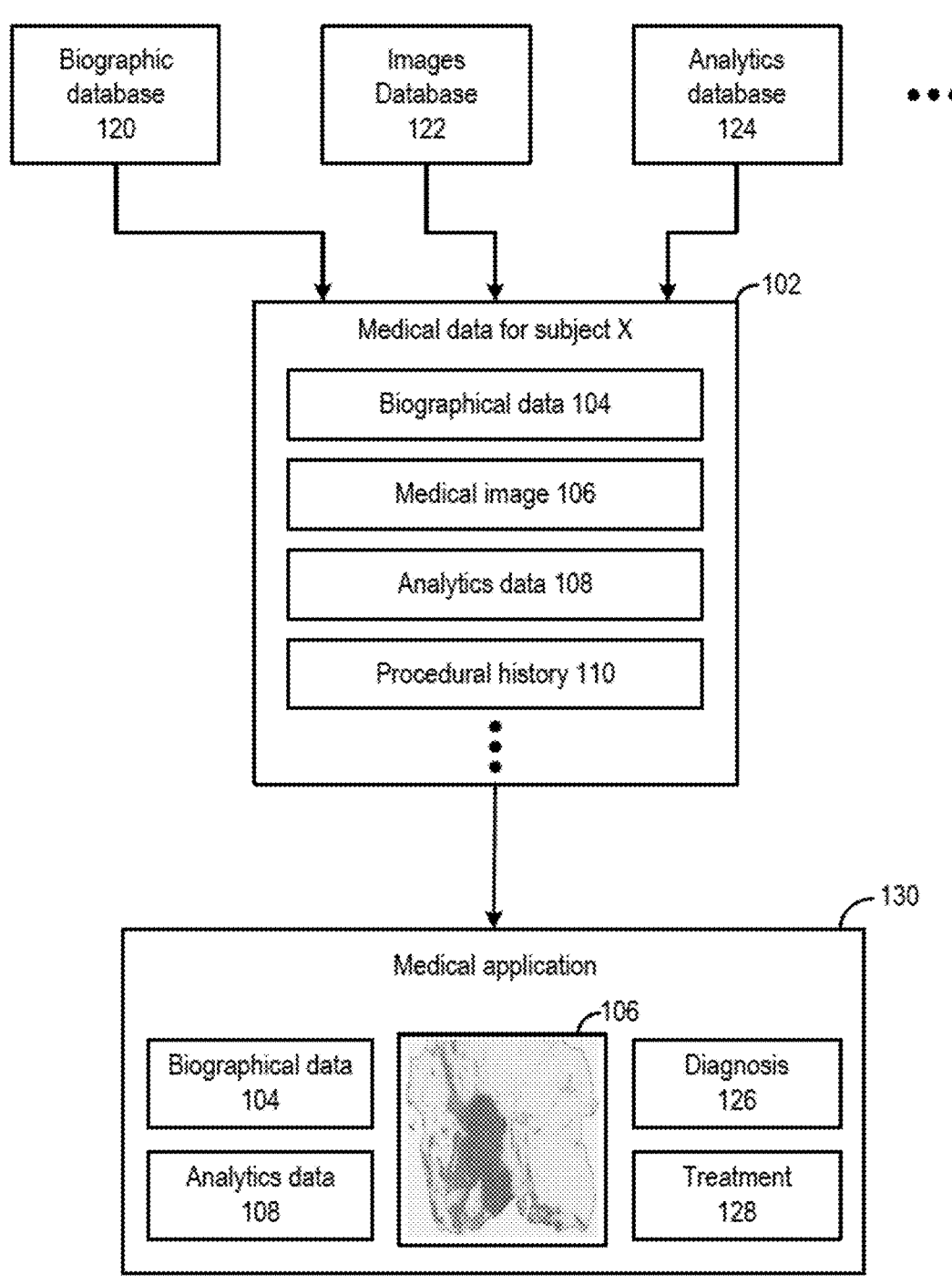
FIG. 1A and FIG. 1B illustrate an example of a clinical process involving multi-modal medical data.

Disclosed herein are techniques for automated verification of multi-modal medical data. Multi-modal medical data of a subject can include multiple categories of medical data of the subject, such as medical images, diagnosis result, biography, etc. The multi-modal medical data can be verified using the disclosed techniques prior to being provided to a medical application. The goal of the verification is to ensure consistency among the different modalities of medical data. For example, if one modality of the medical data indicates a particular cancer type (e.g., lung cancer), the verification can be performed to determine whether the tissue specimen (in the form of a specimen slide) included in the medical images is consistent with the cancer type (e.g., a lung tissue, rather than a liver tissue). The multi-modal medical data can be verified prior to the medical data being accessible on a medical application, such as an oncology workflow application and a multi-disciplinary team collaboration application that hosts a tumor board meeting to ensure that a user of the medical application (e.g., a clinician) is provided with multi-modal medical data that is verified to be consistent among the different modalities.

In some examples, the techniques include receiving, from one or more databases, multi-modal medical data of a subject (e.g., a patient). The databases may include, for example, an EMR (electronic medical record) system, a PACS (picture archiving and communication system), a Digital Pathology (DP) system, an LIS (laboratory information system), and a RIS (radiology information system). The multi-modal medical data can be that of a subject who has (or suspected to have) cancer and can include an medical image of a specimen slide, which can be from a tissue specimen removed from the subject. The multi-modal medical data can also include other modalities, such as analytics data of the tissue specimen. The analytics data may include, for example, a site/location of the tumor, a type of the tissue specimen (e.g., biopsy, resection), or a mutation status of the subject. The multi-modal medical data can also biography information of the subject. Different modalities of the multi-modal medical data can be received from different databases.

The techniques may further include generating a prediction of a biological attribute for the input medical image by using one or more machine learning models and based on the input medical image. The biological attribute may be associated with a type and, for each biological attribute type, there can be a range of biological attributes from which a biological attribute can be predicted for the input medical image. For example, the types of biological attributes can include a type of organ from which the tissue is extracted, and a range of biological attributes for the organ type can include, for example, brain, breast, bronchus and lung, or kidney. The types of biological attributes can also include a type of extraction method of the tissue specimen imaged, and a range of biological attributes for extraction method type can include, for example, biopsy, or resection. Further, the types of biological attribute can also include a type of protein expression, and a range of biological attributes for a protein expression type can include, for example, an epidermal growth factor receptor (EGFR) protein, a KRAS protein, or tumor protein p53. Other types of biological attributes, such as demographical information of the subject (e.g., age, gender, etc.) and clinical information (e.g., a smoking status), and miscellaneous information (e.g., specimen extraction method), etc., can also be predicted.

The predicted biological attribute can then be used to check for consistency between the input medical image and other modalities of the medical data. For example, if a prediction is made that the tissue specimen of input medical image is a lung tissue, a determination can be made about whether other modalities of the medical data are consistent with the predicted biological attribute, such as whether the protein expression is consistent with lung cancer, whether the symptoms exhibited by the subject is consistent with lung cancer, etc. If inconsistency is detected, an indication of a potential misidentification error (e.g., incorrect name listed in the biographic data, the tissue specimen being swapped with another patient, or the analytics data being swapped with those of another patient) can be output in the medical application to warn a user of the medical application that the multi-modal medical data contain potential inconsistencies.

Various techniques of generating the prediction with machine learning models are proposed. In some examples, a machine learning model including an artificial neural network, including a convolutional neural network (CNN) that includes layers to perform convolution operation and a fully-connected layer configured as a classifier, can be used to process the input medical image to perform the prediction. Specifically, the input medical image can include a set of tiles with each tile comprising a block of pixels. The CNN can perform a convolution operation between a tile of the input medical image and a kernel to generate a convolution output for each tile. Based on the convolution output of the tile, the fully connected layer can compute a tile-level prediction output for each tile. The tile-level prediction output may include, for example, the probability of that tile being classified into one of a plurality of candidate biological attributes. For example, in a case where the biological attribute to be predicted is the source organ of a tissue specimen in the input medical image, the plurality of candidate biological attributes can include a plurality of candidate source organs, and one of the candidate source organs is to be selected as the source organ for the tissue specimen.

In some examples, a slide-level prediction of the biological attribute for the input medical image can be made based on aggregating the tile-level prediction outputs. In some examples, the aggregation can be based on a voting mechanism. Specifically, tiles having a particular tile-level prediction output can be counted, and the tile counts for different tile-level prediction outputs can be obtained. A slide-level prediction can be made based on the tile-level prediction output having the maximum tile counts. For example, if the tile-level prediction output associated with a majority of the tiles indicate that the source organ is a lung, a slide-level prediction can be made that the source organ of the specimen slide of the input medical image is from the lung. In some examples, each tile can be assigned a scaling factor or a weight (e.g., between 0 and 1), and the tile count for each tile-level prediction output can be based on a sum of the scaling factors of the tiles having that tile-level prediction output. The scaling factor of a tile can reflect, for example a confidence level of the tile-level prediction of the tile, or a degree of relevance of the tile-level prediction of the tile. The confidence level can be based on the probability of the tile having a particular biological attribute as indicated by the tile-level prediction output with a higher probability lead to a higher confidence level and vice versa. Moreover, the degree of relevance can be based on, for example, a location of the tile within the medical image, or a distance of the tile from the expected locations of tissue/tumor cells that can identify the source organ. With such arrangements, the influence of certain tiles that are less relevant or produce low-confidence tile-level predictions can be reduced, which can improve the likelihood that the voting mechanism generates an accurate slide-level prediction.

Techniques of training the CNN are also proposed. In one example, the CNN can be trained based on a weakly-supervised training operation. As part of the training operation, the CNN can receive training medical images as input. In some examples, each tile of a training medical image can be associated with a label. Through the training operation, the coefficients of the kernel can be adjusted to maximize the matching between the tile-level prediction outputs of each tile of the training medical images and the labels of the tiles. In some examples, each training medical image is associated with a label indicating the biological attribute of the medical image (e.g., a particular organ type, a particular tissue specimen extraction method, or a particular protein expression). Moreover, different sets of training medical images, with each set associated with a different type of label (e.g., organ type, extraction method, protein expression, gender, etc.)., can be used to train different sets of weights of the CNN to predict different types of biological attributes. For example, a set of training medical images associated with labels pertaining to different tissues types can be used to train the CNN to predict a type of tissue, whereas another set of training medical images associated with labels pertaining to different disease type can be used to train the CNN to predict a type of disease. The training can be part of a multiple instance learning (MIL) where a weak label is applied to a whole bag of instances with each tile being an instance. Through the training operation, the coefficients of the kernel can be adjusted to maximize the matching between the labels of the medical images and the slide-level predictions generated by the CNN for the medical images. With a weakly supervised training operation, the labeling of the training medical images can be performed at the image level rather than at the tile level. Such arrangements can reduce the effort involved in labeling the medical images which, in turn, allows a large volume of labeled medical images to be made available to improve the training of the CNN. To perform a prediction of a biological attribute, a set of weights of the CNN associated with a particular type of biological attribute to be predicted can then be retrieved, and can be combined with the pixel data of the tiles of the input medical image to perform the prediction.

In some examples, a slide-level prediction of the biological attribute for the input medical image can be made based on inputting a slide-level representation of the input medical image to a machine learning model to generate the prediction. The slide-level representation can include a multi-dimensional vector with each dimension representing a feature, and the slide-level representation can include a set of feature values representing a signature of the input medical image, while the signature can be used to predict the biological attribute (e.g., source organ, extraction method, or protein expression.) of the input medical image. In some examples, the slide-level representation can include feature values of multiple medical images of the same specimen slide obtained at different magnifications. With such arrangements, high resolution features of the specimen slide from a first medical image of a higher magnification, as well as more numerous features of the specimen slide from a second medical image of a lower magnification (which can be a different image from the first medical image, or can be the same image as the first medical image but of a different magnification level), can be included in the slide-level representation, such that the slide-level representation can provide a more complete yet detailed representation of various features (e.g., cell structures) of the specimen slide.

The set of feature values can be input to a machine learning model to generate a slide-level prediction of the biological attribute. In some examples, the machine learning model can include a gradient-boosted decision trees each configured to generate a prediction decision based on a different subset of the features of the slide-level representation, and the slide-level prediction can be made based on, for example, the prediction decision of a majority of the decision trees.

In some examples, the slide-level representation can be generated based on tile-level representations generated for each tile of the input medical image. In some examples, the tile-level representation can include an embedding generated based on inputting pixels of a tile into a fully-connected neural network. The embedding can be a multi-dimensional vector. The embedding can provide a mapping of discrete categorical variables into a vector of continuous numbers in an embedding space. The discrete categorical variable can represent, for example, the absence or presence of a feature of the tile. Through the mapping, a vector having a reduced dimensionality, compared with the number of discrete categorical variables, can be used to represent a tile. Moreover, the mapping can be performed by a deep neural network, which can be trained using supervised techniques to generate embedding vectors for the tiles such that tiles having the same biological attribute are represented by embedding vectors that are closer in the embedding space than those tiles having different biological attributes. In some examples, a machine learning model trained using unsupervised techniques can also be used to generate the embedding vectors. As such, each tile can be represented by an embedding vector that emphasizes relevant features that distinguish between tiles of different biological attributes and deemphasizes features that are common among the tiles or features that are not related to the biological attributes to be predicted.

In some examples, the slide-level representation can be generated based on comparing the tile-level representations ("input tile-level representations") generated for the tiles of the input medical image with reference tile-level representations of a plurality of clusters of reference tiles from a plurality of reference medical images. The reference medical images can have different biological attributes for a particular biological attribute type (e.g., different source organs, different extraction methods, and different protein expressions). Specifically, reference tile-level representations, which can include embedding vectors, can be generated from tiles of reference medical images using the same trained fully-connected neural network. The reference tile-level representations can be clustered into multiple clusters based on various clustering algorithms, such as k-means clustering. Each cluster can represent a feature/dimension in the slide-level representation. A feature value of a feature in the slide-level representation can be based on a number of tiles of the input medical image being in the cluster representing the feature. In some examples, the feature value can be based on a fraction or a decimal number representing a ratio between the number of tiles in the cluster and the total number of tiles of the input medical image. As such, the slide-level representation can represent a distribution of the tiles, represented by the input tile-level representations, in the plurality of clusters of reference tiles. The distribution can input to the machine learning model (e.g., gradient-boosted decision trees) to generate the slide-level prediction of the biological attribute for the input medical image.

In some examples, the slide-level representation of the input medical image can also be used to support other applications. In some examples, the slide-level representation can be used to perform a similarity search for medical images that are similar to the input medical image. The medical images being searched can include reference medical images used to generate the clusters of reference tile-level representations which, in turn, are used to generate the slide-level representation of the input medical image, as described above, as well as other medical images. These medical images, as well as their slide-level representations, can be stored in a database. The medical images can also be associated with the medical data (e.g., diagnosis results and treatment history) of the subjects in the database. A similarity search can be performed based on finding vectors of slide-level representations that have the shortest distance (e.g., Euclidean distance) from the vector of the slide-level representation of the input medical image to retrieve medical images having similar slide-level representations as the input medical image, as well as the medical data associated with the medical images.

The medical images and medical data obtained from the similarity search can support various applications. For example, the biological attributes of the medical images can be used to verify the predicted biological attribute of the input medical image, based on the fact that the slide-level representations of those medical images are similar to each other and the images are likely to have the same biological attribute. As another example, the multi-modal medical data, such as treatment history, of the subjects of those medical images can also provide useful information used to support a clinical decision for the subject of the input medical image.

In some examples, the slide-level representation can also be used to train a machine learning model (e.g., decision trees) to perform a prediction of a diagnosis of the subject. The diagnosis may include, for example, a type of tumor (e.g., a brain tumor, a liver tumor, etc.). The predicted diagnosis support various applications, such as a clinical decision of a treatment for the subject, to verify the diagnosis of the subject included in the multi-modal medical data of the subject, etc.

The use of slide-level representation, which represents the overall input medical image, to predict the biological attribute of the input medical image can further improve the accuracy of prediction. As explained above, performing tile-level prediction for each individual tiles and then aggregating the tile-level predictions to generate a slide-level prediction can be performed by a machine learning model trained using a weakly-supervised training operation. But such training operation may lead to a less accurate prediction, as each medical image is associated with a weak label, which can reduce the rate of adjustment of the parameters of the machine learning model in a case of a mismatch between the prediction and the label. Moreover, a weak label may be used to account for the different types of cells that may be present in a tissue, and tissues of different organs may have the same type of cells and different types of cells (e.g., tumor cells) that distinguish different between different organs, which can lead to tiles of the same medical image being predicted to have different biological attributes.

On the other hand, a machine learning model (e.g., gradient-boosted decision trees) can be trained using slide-level representations of reference medical images. Moreover, as the slide-level representation of a reference medical image is based on a distribution of tiles in clusters of reference tiles, which represents a relationship between the tile-level representations of the input medical image and reference tile-level representations of the reference medical images, and each tile-level representation can include an embedding vector that emphasizes relevant features that distinguish between tiles of different biological attributes and deemphasizes features that are common among the tiles or features that are not related to the biological attributes to be predicted, the slide-level representation can contain more complete and relevant information of the entire medical image that can be used to distinguish between medical images of different biological attributes. As a result, each slide-level representation can be associated with a label, and the rate of adjustment of the parameters of the machine learning model in a case of a mismatch between the prediction and the label can be increased compared with a case where the images are associated with weak labels. This can improve the likelihood of the machine learning model in predicting the correct biological attribute for the input medical image.

The disclosed techniques enable automated verification of multi-modal medical data, as well as flagging of potential inconsistencies in the medical data. This can reduce the likelihood of a clinician making a clinical decision for a patient based on medical data of another patient due to undetected identification error. Moreover, the similarity search using slide-level representation can also support various applications, such as verifying the predicted biological attribute of the input medical image, as well as obtaining useful information, such as treatment history and diagnoses of other subjects who may have similar medical conditions as the subject, to support a clinical decision for the subject. All these can improve quality of care.

I. Example Clinical Process Involving Multi-Modal Medical Data

Figure 1B:
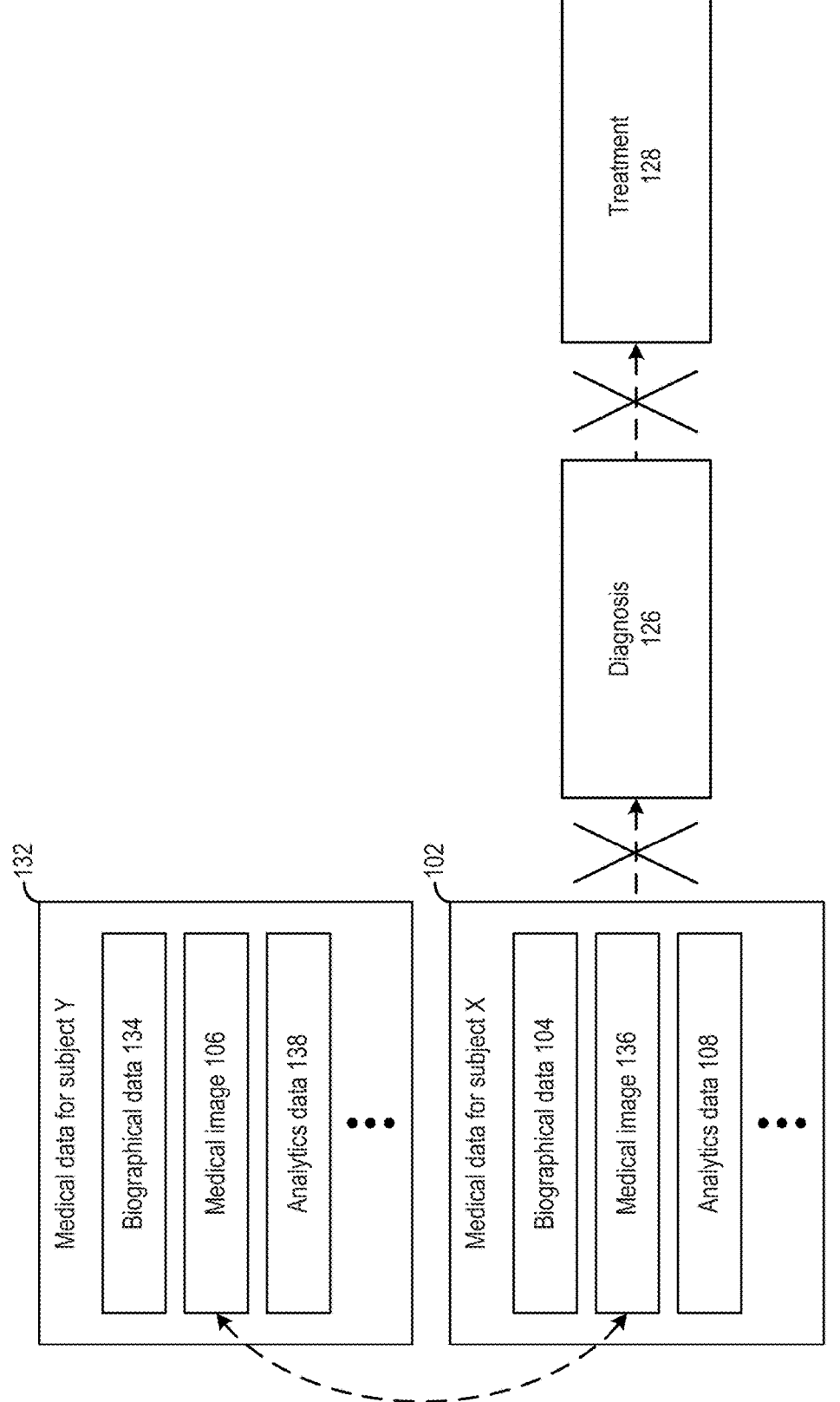

FIG. 1A and FIG. 1B illustrate examples of a clinical process 100 involving multi-modal medical data. As shown in FIG. 1A, multi-modal medical data 102 is of a subject X. As shown in FIG. 1A, multi-modal medical data 102 may include biographical data 104, a medical image 106, analytics data 108, etc. Biographical data 104 can include various personal information of the patient, such as name, gender, age, ethnicity, etc. Medical images 106 can include images of a tissue specimen of the patient which has been stained to reveal various information. For example, in a case where the tissue specimen is stained with Hematoxylin and Eosin (H&E), medical images 106 can reveal cell structures of the tissue specimen which can include a tumor. Moreover, in a case where the tissue specimen is processed with immunostaining, medical images 106 can reveal the presence/absence of certain protein(s) in the tissue specimen, which can indicate a certain type of gene mutation. Analytics data 108 can divulge various information related to medical images 106, such as its extraction method (e.g., biopsy versus resection), a site/location of a tumor (e.g., lung, brain, breast, ovary, or kidney) represented in medical images 106, and a status of gene mutation revealed in medical images 106. Procedural history 110 can indicate a history of medical procedures received by subject X, including the procedures involved in the extraction of tissue specimens. For example, in a case where subject X receives a surgical resection procedure to remove the tissue specimen including a tumor, the resection procedure can be included as part of the treatment history of subject X.

Multi-modal medical data 102 are typically assembled from multiple data sources and prepared by different health care providers. For example, biographic data 104 can be prepared by a patient intake department, medical image 106 can be prepared by a medical imaging department, whereas analytics data 108 can be prepared by analysts in a histology department. Each of these departments may have its own database to store the data. For example, biographic database 120 can store biographic data, images database 122 can store medical images, whereas analytics database 124 may store image analytics data. Databases 120, 122, and 124 may include, for example, an EMR (electronic medical record) system, a PACS (picture archiving and communication system), a Digital Pathology (DP) system, an LIS (laboratory information system), and a RIS (radiology information system).

From databases 120, 122, and 124, biographic data 104, medical images 106, and analytics data 108 can be retrieved for a patient and assembled into multi-modal medical data 102, which then be provided to a medical application 130, such as an oncology workflow application or a multi-disciplinary team collaboration application that hosts a tumor board meeting. As shown in FIG. 1A, medical application 130 can display biographical data 104, medical images 106, and analytics data 108 to the participants of the tumor board meeting, including clinicians. Based on these data, the clinicians can determine diagnosis 126 and treatment 128 for subject X. For example, based on medical image 106 and analytics data 108, the clinicians can determine a type of the cancer (e.g., breast cancer, brain cancer, ovarian cancer), the size of the tumor, and a stage of cancer the patient is in as part of diagnosis 126. The clinicians can also determine treatment 128 (e.g., chemotherapy, radiation, surgery) the patient should receive to prolong the survival of the patient based on diagnosis 126. In addition, the clinicians may consider the mutation status of the patient, which can be part of analytics data 108, in determining a treatment. For example, if subject X has breast cancer and carries mutations in the BRCA1 and BRCA2 genes, the clinicians may determine that subject X may have higher response rates to induction chemotherapy and radiotherapy and include induction chemotherapy and radiotherapy in treatment 128 for subject X as a result.

The process of collection of different modalities of medical data by different parties followed by assembly of those data into multi-modal medical data 102 can be prone to error. For example, identification errors can be introduced to the multi-modal medical data, where some or all of the medical data of a particular patient is swapped with those of another patient. FIG. 1B illustrates an example source of identification error. In FIG. 1B, specimen provenance complication (also known as misattribution) can occur, in which the tissue specimen (or its image) of one patient has been swapped with another patient. Misattribution can occur at any stage from when the tissue specimen is collected to when the specimen image is assembled into multi-modal medical data 102. For example, the tissue specimen can be swapped at the laboratory where the specimen is collected and/or at the imaging department where an image of the specimen is taken. Moreover, the medical image of the tissue specimen can also be swapped. Further, analytics data can also be swapped. Note that the detection of misidentification errors may be done at different levels of the data such as the meta-data but also on the raw data itself. As there are many sources of misidentification errors, the meta-data might not belong to the correct medical data.

Due to these identification errors, multi-modal medical data 102 may include medical data, such as medical image 106 and analytics data 108 that do not belong to subject X. For example, in FIG. 1B, medical image 106 of subject X is swapped with medical mage 136 of medical data 132 of subject Y, which further include biographical data 134 and image analytics data 138 of subject Y. The identification error can also cause inconsistency among multi-modal medical data 102. For example, the multi-modal medical data of a male patient may have an image showing an ovarian cancer tumor. As another example, the multi-modal medical data of a patient may include an image showing a brain tissue, but the analytics data indicate that the patient has lung cancer.

Undetected identification errors can degrade clinical care if a clinical decision (e.g., a diagnostic decision or a treatment decision) made for a patient is based on medical data of another patient. For example, due to the identification errors, the clinician may generate incorrect diagnosis 126 indicating that subject X has lung cancer when, in fact, the patient has brain cancer. In addition, the clinician may determine incorrect treatment 128 for subject X based on incorrect diagnosis 126. As a result, subject X does not receive the treatment he/she needs for the brain cancer but instead receives an unnecessary treatment that can harm subject X in other ways.

II. Example Medical Data Checker System

A. System Overview

Figure 2A:
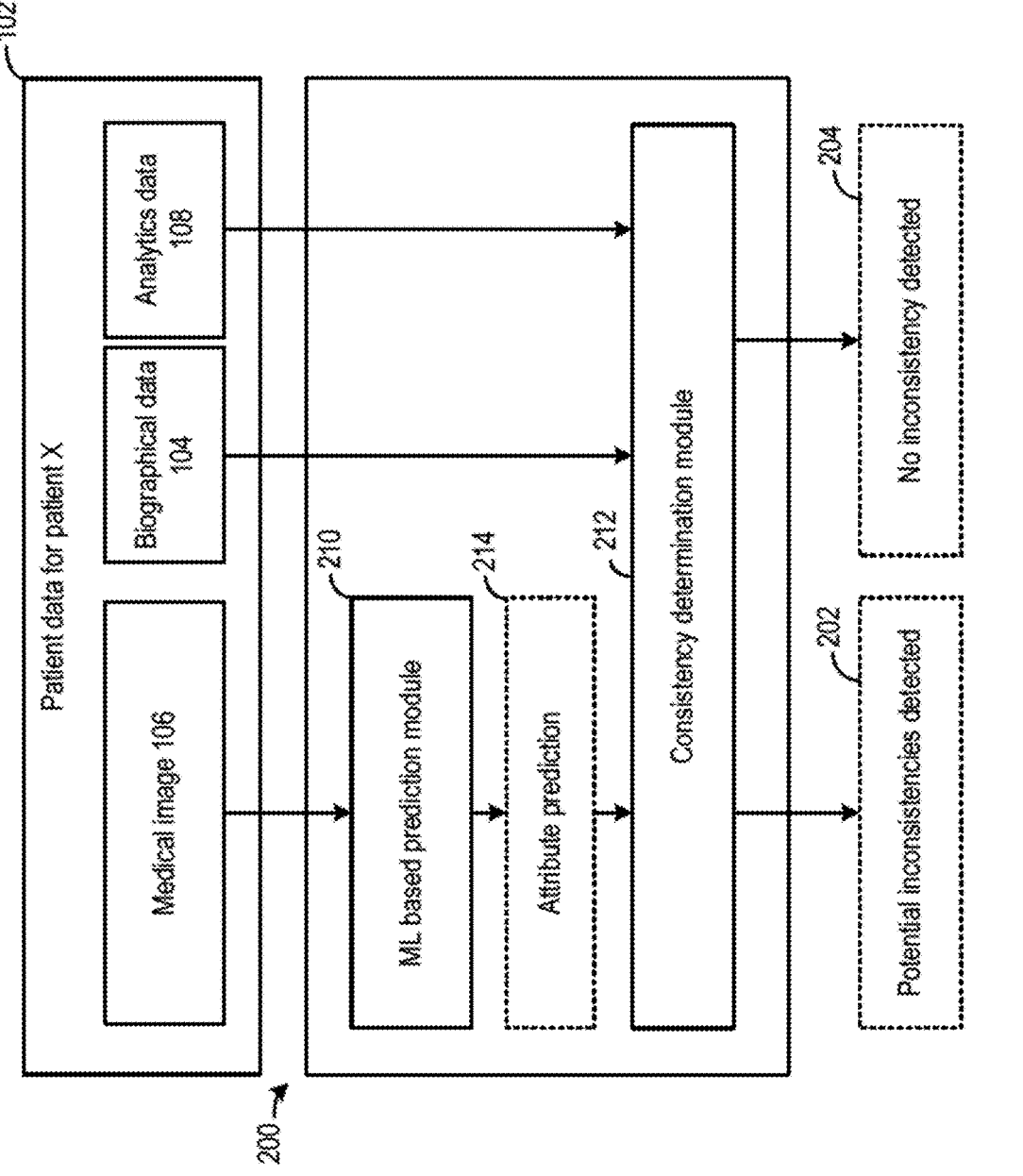
FIG. 2A and FIG. 2B illustrate an example of a medical data checker system that can be used in the example clinical process of FIG. 1A and FIG. 1B, according to certain aspects of the present disclosure.
Figure 2B:
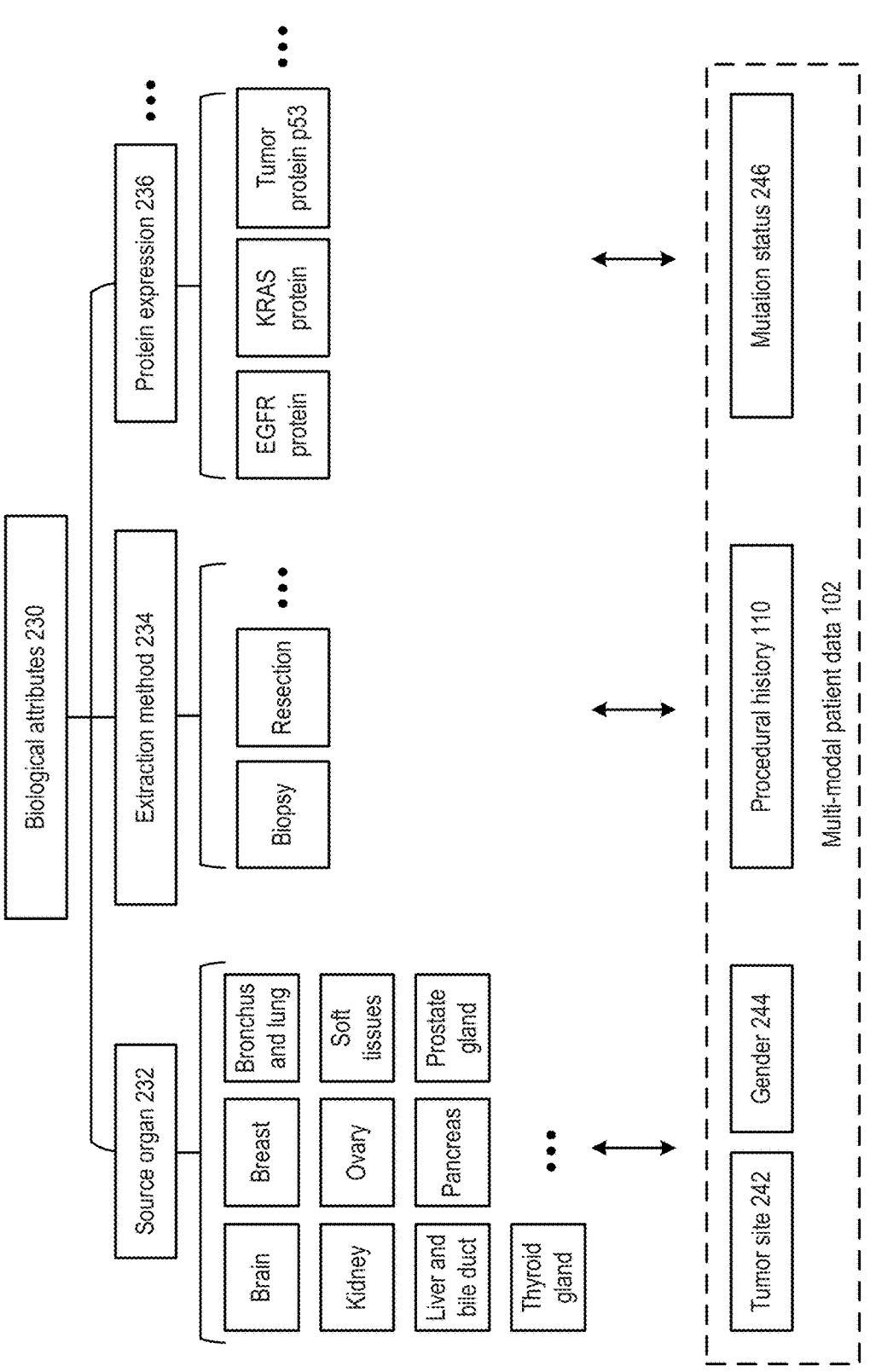

FIG. 2A and FIG. 2B illustrate an example medical data checker system 200 that can address at least some of the issues above. Medical data checker system 200 can receive multi-modal medical data, such as multi-modal medical data 102 including medical image 106, biographical data 104, and analytics data 108, and can determine consistency among the different modalities of medical data. If inconsistency is detected, medical data checker system 200 can output an indication 202 of the detected inconsistency and the source of inconsistency, otherwise medical data checker system 200 can output an indication 204 that no inconsistency is detected. In some examples, medical data checker system 200 can be part of medical application 130 to warn users of the application that the multi-modal medical data presented in the application contains potential inconsistencies and further investigation may be needed before the users can make clinical decisions based on multi-modal medical data 102.

Referring to FIG. 2A, medical data checker system 200 includes a machine learning (ML) based prediction module 210 and a consistency determination module 212. Prediction module 210 can include one or more machine learning models that can receive medical image 106 of a specimen slide, which can be prepared from a tissue specimen removed from a subject and generate a prediction 214 of a biological attribute. The biological attribute may include, for example, a type of organ from which the tissue is extracted (e.g., brain, lung, breast, or kidney), an extraction method of the tissue (e.g., biopsy or resection), or a protein expression. Medical image 106 can include a set of tiles with each tile comprising a block of pixels. As to be described below, in some examples, prediction module 210 can perform a tile-level prediction of the biological attribute for each tile of medical image 106 using a machine learning model and then generate a slide-level prediction of the biological attribute for medical image 106 based on aggregating the tile-level predictions. In some examples, prediction module 210 can also generate a slide-level representation of medical image 106 using a first machine learning model and input the slide-level representation to a second machine learning model to generate the slide-level prediction of the biological attribute for medical image 106.

Prediction module 210 can be configured to generate prediction 214 from medical image 106 for different types of biological attributes. Prediction 214 can then be provided to consistency determination module 212 to be checked against the other modalities of medical data to detect inconsistencies. FIG. 2B illustrates examples of types of biological attributes 230 and a range of biological attributes for each biological attribute type that can be predicted by prediction module 210. A predicted biological attribute of a particular type can be checked against other modalities of medical data by consistency determination module 212. As shown in FIG. 2B, prediction module 210 can be trained to predict, based on medical image 106, types of biological attributes including a source organ 232, an extraction method 234, a protein expression 236, etc.

Specifically, source organ 232 can indicate the type of organ from which the tissue specimen (prepared as specimen slide and imaged in medical image 106) is extracted. A range of organ types that can be predicted from medical image 106 may include, for example, brain, bronchus and lung, breast, ovary, soft tissues, liver and bile duct, pancreas, prostate gland, or thyroid gland. The prediction can be based on detecting, from medical image 106, image features of cell structures specific for different organs, such as cup-shaped alveolus cells for lung, neuron cells for brain, or cardia muscle cells for heart. A prediction of source organ 232 can be checked against other modalities of data, such as tumor site 242 of analytics data 108 and gender 244 of biographic data 104, to detect potential inconsistency. For example, if the prediction of source organ 232 indicates a type of organ different from tumor site 242 and/or inconsistent with gender 244 of the patient, consistency determination module 212 can indicate that a potential inconsistency in tumor site information and/or gender information is detected.

In addition, extraction method 234 can indicate the procedure involved in extracting the tissue sample. A range of extraction methods can include a biopsy procedure, a resection procedure, etc. A biopsy procedure typically involves a focused removal of a small amount of tissue with a needle, whereas a resection procedure involves surgical removal of a relatively large amount of tissue. Common needle biopsy procedures can include, for example, fine-needle aspiration and core needle biopsy. A hollow needle biopsy tissue typically has a different shape (e.g., circular shape) from a tissue obtained from resection. Moreover, due to the focused removal procedure, a biopsy tissue typically has a larger percentage of tumor cells than a resection tissue. Therefore, a prediction of whether a tissue specimen captured in medical image 106 is obtained by a biopsy procedure or by a resection procedure can be based on analyzing the image to determine, for example, the shape of the tissue and a percentage of tumor cell in the specimen. The prediction can be checked against, for example, procedure history 110 to detect potential inconsistency. For example, if the prediction of extraction method 234 indicates that the tissue is obtained using resection but procedure history 110 indicates that the user has not undergone any surgical procedure, and that user has recently undergone hollow needle biopsy, consistency determination module 212 can indicate that a potential inconsistency in procedural history 110 is detected.

Further, protein expression 236 can indicate presence of certain proteins that are indicative of gene mutation. Protein expression 236 can be predicted based on analyzing an image of a tissue specimen that has undergone immunostaining to identify proteins in cells of a tissue. One example of immunostaining is immunohistochemistry (IHC), which exploits the principle of antibodies binding specifically to antigens to selectively identify proteins in cells of a tissue specimen. A range of protein expressions 236 that can be predicted from the image can include, for example, epidermal growth factor receptor (EGFR) protein, KRAS protein, tumor protein p53, PD-L1, or HER2. The predicted protein expressions can be analyzed to determine whether there are gene mutations. The prediction can be checked against, for example, mutation status 246 which can be part of analytics data 108. If the prediction indicates a particular type of gene mutation (e.g., EGFR mutation, KRAS mutation, TP53 mutation, increased PD-L1 expression, or HER2 mutation) in the patient but that gene mutation type is not listed in mutation status 246, consistency determination module 212 can indicate that a potential inconsistency in mutation status 246 is detected.

Besides source organ 232, extraction 234, and protein expression 236, other types of information can be predicted by prediction module 210. For example, biological attributes such as demographic information of the subject (e.g., age, gender, etc.), clinical information such as a habit of the subject (e.g., a smoking status), a state of a disease of the subject, type of tumor, etc., can be predicted by prediction module 210. For example, cell features that are indicative of aging and smoking can be detected from the medical image, and the age and the smoking status of subject can be predicted based on the cell features. The prediction may include a real number (e.g., 46.6 years old), an integer, or a category (e.g., between 31-35 years old). As another example, the gender of the subject can also be predicted based on the type of source organ of the specimen slide. It will be appreciated that the predicted biological attribute/clinical information can take on any form, including real number, binary output, category, etc.

B. Tile-Level Predictions and Aggregation

Figure 3A:
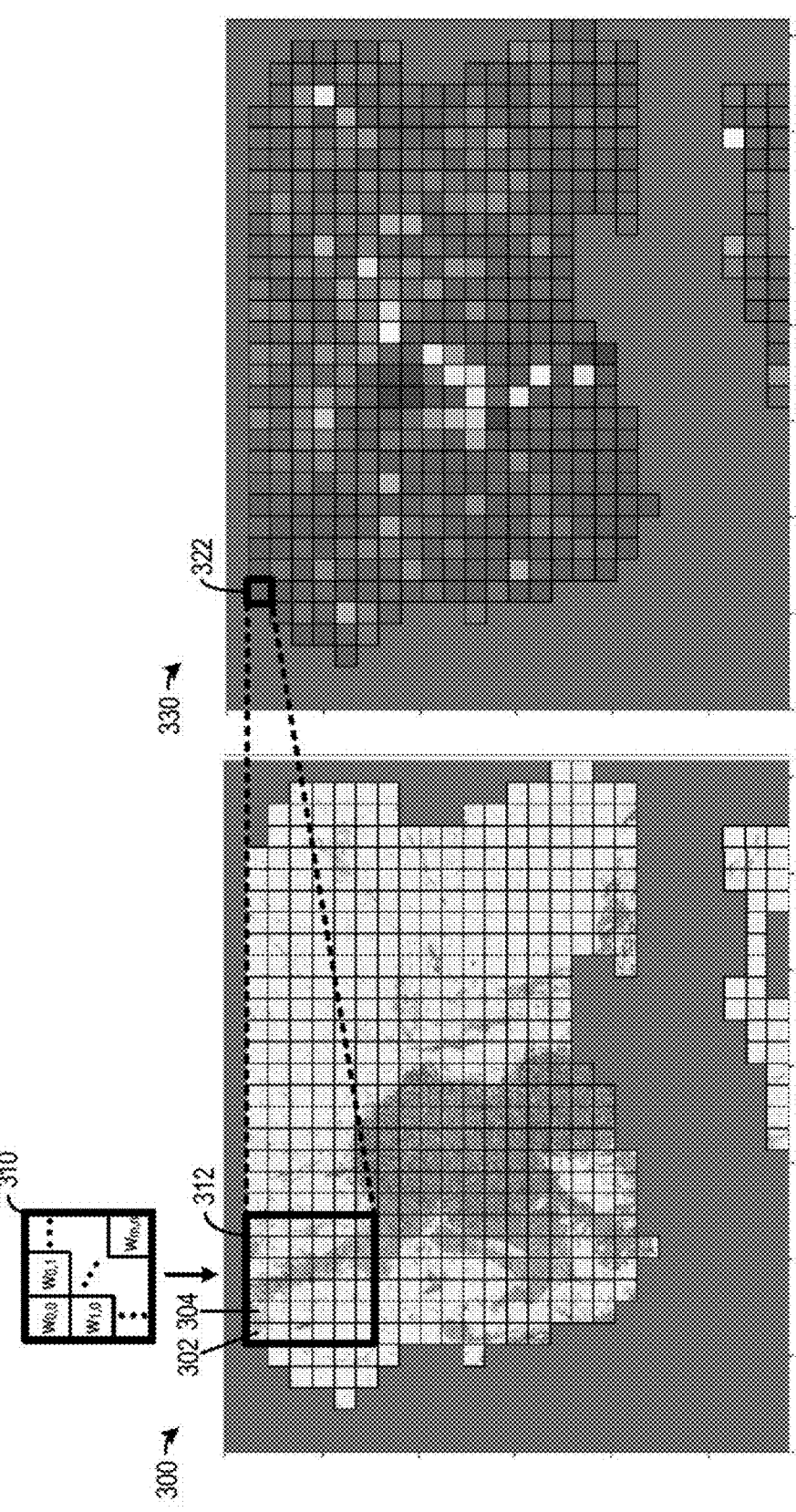
Figure 3B:
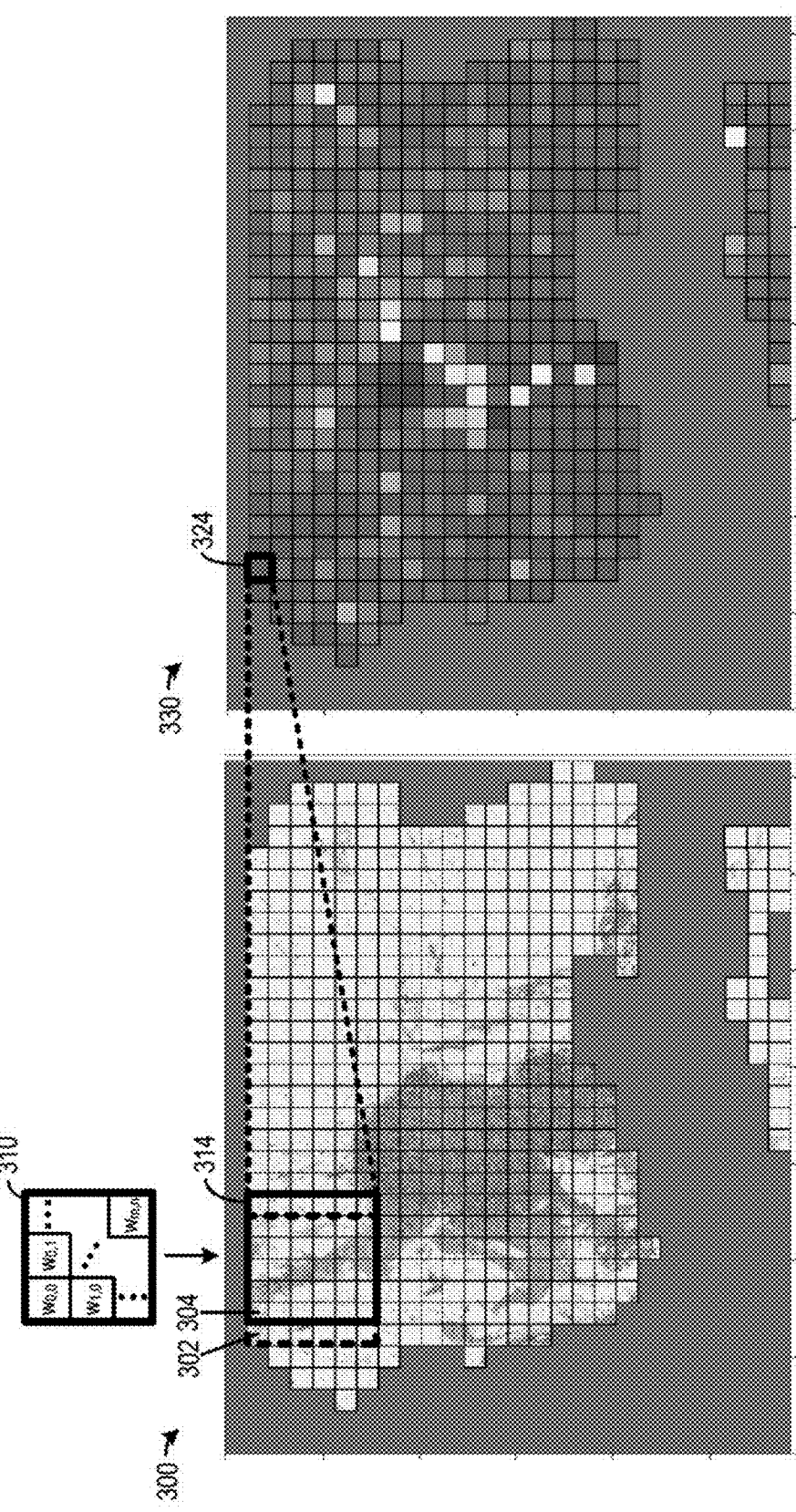

FIG. 3A, FIG. 3B, and FIG. 3C illustrate an example of prediction operations of prediction module 210. Referring to FIG. 3A, the pixels of a medical image 300 can be divided into tiles, such as tiles 302 and 304. Each tile can include a block of pixels of medical image 300. In one example, a tile can include 224×224 pixels. A convolution operation can be performed between medical image 300 and a kernel 310. Kernel 310 can represent a pattern of image features, such as features of cells of a type of organ, a type of extraction method, and a protein expression, to be detected from medical image 106. Kernel 310 can include an array of weights, including weights w0,0, w0,1, w1,0, wm,n, etc., with each weight corresponding to a pixel and representing part of the image features to be detected, and kernel 310 can span a set of tiles of pixels. As to be described below, the weights of kernel 310 can be learnt from training operations to detect different image features to support a prediction of a type of organ, a type of extraction method, a protein expression, etc., where different sets of weights of kernel 310 are trained using different sets of training medical images, with each set associated with a different type of label (e.g., organ type, extraction method, protein expression, etc.).

Referring to FIG. 3A, a convolution operation can be performed, in which kernel 310 can be superimposed over a set of tiles, such a set of tiles 312, which includes tiles 302 and 304 as well as other tiles. A convolution output can be computed for tile 302 based on multiplying the weights of the kernel with a corresponding pixel within the set of tiles and summing the products. The convolution output for a set of tiles can represent, for example, a correlation between the pixels of the set of tiles and the target image features. The convolution output can be computed as follows:

$$c_{e,f} = \sum_{r=0}^{R-1} \sum_{s=0}^{S-1} p_{eD+r, fD+s} \times W1_{r,s} \qquad \text{(Equation 1)}$$

In Equation 1, W1 represents the weight of kernel 310, p represents a pixel value, whereas c represents a convolution output. The indices e and f represent the coordinates of the convolution output c in a convolution output tensor. Moreover, the indices r and s can define the coordinates of the pixels that are superimposed by the weights of kernel 310 for the convolution operation. A convolution output can be computed based on an array of pixel values superimposed by the kernel. The kernel can be shifted over another set of pixel values with each set separated by a distance D. A convolution output tensor including multiple convolution outputs c can then be computed for a tile, such as tile 302 in FIG. 3A.

The convolution output tensor computed from a set of tiles can be further processed by a classifier to generate a tile-level prediction of a biological attribute for the tile as follows:

$$\text{Prediction}_{tile} = f\left(\sum_{e=0}^{E-1} \sum_{f=0}^{F-1} c_{e,f} \times W2_{e,f}\right) \qquad \text{(Equation 2)}$$

In Equation 2, each convolution output of the convolution output tensor can be multiplied with another weight W2, the products are summed, and the sum can be processed by an activation function f to generate a tile-level prediction output. Weight W2 can define the contribution of each convolution output c to the tile-level prediction for the tile. In FIG. 3A, a tile-level prediction output 322 can be computed for tile 302. The purpose of the activation function is to introduce non-linearity into the prediction output to simulate a decision of whether to activate a neuron. Examples of activation function can include ReLU, a sigmoid function, and a softmax function. The prediction output from Equation 2 can represent, for example, the probability of the tile having a certain biological attribute, such as a particular source organ 232, a particular extraction method 234, or a particular protein expression 236. In some examples, multiple prediction outputs, each for a candidate biological attribute, can also be computed for a tile using Equation 2 and using different weights W2. For example, in a case where a prediction of source organ is made, the probabilities of the tile having a source organ of a brain, a breast, a bronchus and lung, a kidney, an ovary, a soft tissue, etc., as listed in FIG. 2B, can be computed for the tile.

Referring to FIG. 3B, another convolution operation can be performed over another set of tiles 314 to compute convolution outputs and a tile-level prediction output 324 for tile 304, and the process can be repeated until the tile-level predictions are generated for all tiles of medical image 300. An array 330 of tile-level prediction outputs can be obtained, which can represent, for example, a distribution of probabilities of a tile having a particular biological attribute among the set of tiles of medical image 300.

The tile-level prediction outputs generated from medical image 300 can be aggregated to generate a slide-level prediction for medical image 300. In some examples, the aggregation can be based on a voting mechanism. Specifically, tiles having a particular tile-level prediction output can be counted, and the tile counts for different tile-level prediction outputs can be obtained. A slide-level prediction can be made based on the tile-level prediction output having the maximum tile counts.

FIG. 3C illustrates examples of aggregating the tile-level prediction outputs based on a voting mechanism. As shown in FIG. 3C from array 330, groups of tiles 334 and 336 of medical image 300 can be determined to have higher probabilities of being classified as part of a breast than being classified as part of a lung. As a result, groups of tiles 324 and 326 can be classified as part of a breast. Moreover, the rest of the tiles of medical image 300 can be determined to have higher probabilities of being classified as part of a lung than being classified as part of breast and can be classified as part of a lung as a result.

A slide-level prediction for a biological attribute of medical image 300, such as prediction 214 of FIG. 2A, can be made based on the tiles having a particular tile-level prediction output, and the tile counts for different tile-level prediction outputs can be obtained. A slide-level prediction can be made based on the tile-level prediction output having the maximum tile counts. For example, referring to table 340, it can be determined that 20 tiles have a tile-level prediction output as part of a breast, while 100 tiles have a tile-level prediction output as part of a lung. Notice that the number of tiles in table 340 are provided for illustration purpose only. A prediction that medical image 300 is of a tissue specimen of a lung can then be made based on the number of tiles being classified as part of a lung (100) far exceeding the number of tiles classified as part of a breast (20) which include groups of tiles 334 and 346.

As another example, each tile can be associated with a weight/scaling factor (0-1). The scaling factor of a tile can reflect, for example, a confidence level of the tile-level prediction of the tile or a degree of relevance of the tile-level prediction of the tile. The confidence level can be based on, for example, a difference between the probability of the selected candidate biological attribute and the probabilities of other candidate biological attributes not selected for the tile. A larger difference can indicate a higher confidence level, whereas a smaller difference can indicate a smaller confidence level. Moreover, the degree of relevance can be based on, for example, a location of the tile within the medical image or a distance of the tile from the expected locations of tissue/tumor cells that can identify the source organ. With such arrangements, the influence of certain tiles that are less relevant or produce low-confidence tile-level predictions can be reduced, which can improve the likelihood that the voting mechanism generates an accurate slide-level prediction.

For example, in FIG. 3C, the tile-level prediction outputs of groups of tiles 334 and 336 can be associated with a larger weights due to, for example, groups of tiles 334 and 336 being at expected locations of breast cancer cells and are therefore more relevant in predicting the source organ of the slide specimen. The tile-level prediction outputs of groups of tiles 334 and 336 can also be associated with a high confidence level due to the high probabilities of the tissue specimen in the groups of tiles coming from the breast. Referring to table 350, instead of counting each tile as one, a sum of the scaling factors/weights of the tiles for each tile-level prediction output can be obtained. As a result, when considering the scaling factors, the total count of tiles classified as part of a breast can become higher than the count of tiles classified as part of a lung. A prediction that medical image 300 is of a tissue specimen of a breast can then be made as a result.

C. Machine Learning Models to Support Tile-Level Predictions and Aggregation

Figure 4A:
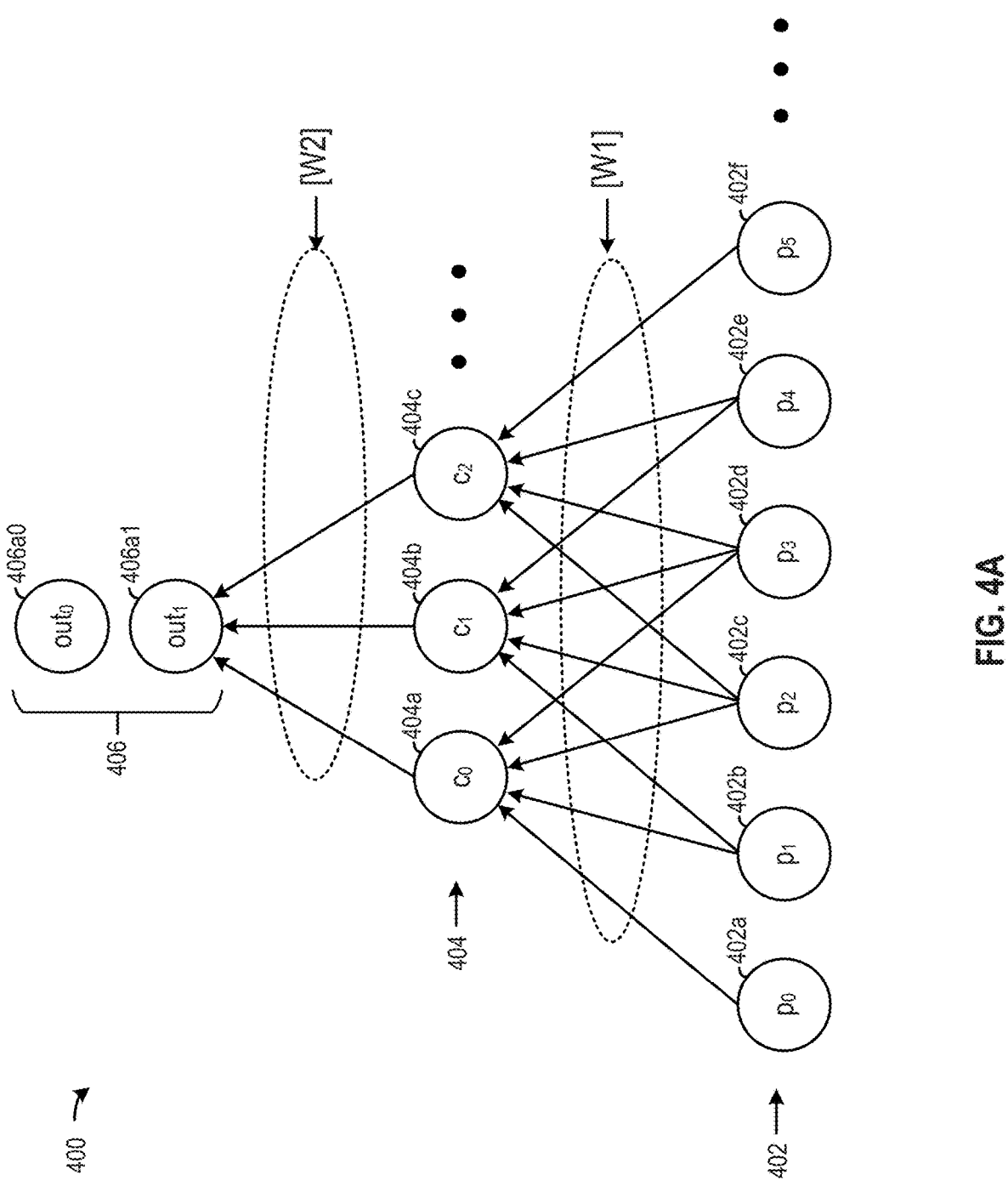
FIG. 4A and FIG. 4B illustrate example components of medical data checker system of FIG. 2A and FIG. 2B, according to certain aspects of this disclosure.
Figure 4B:
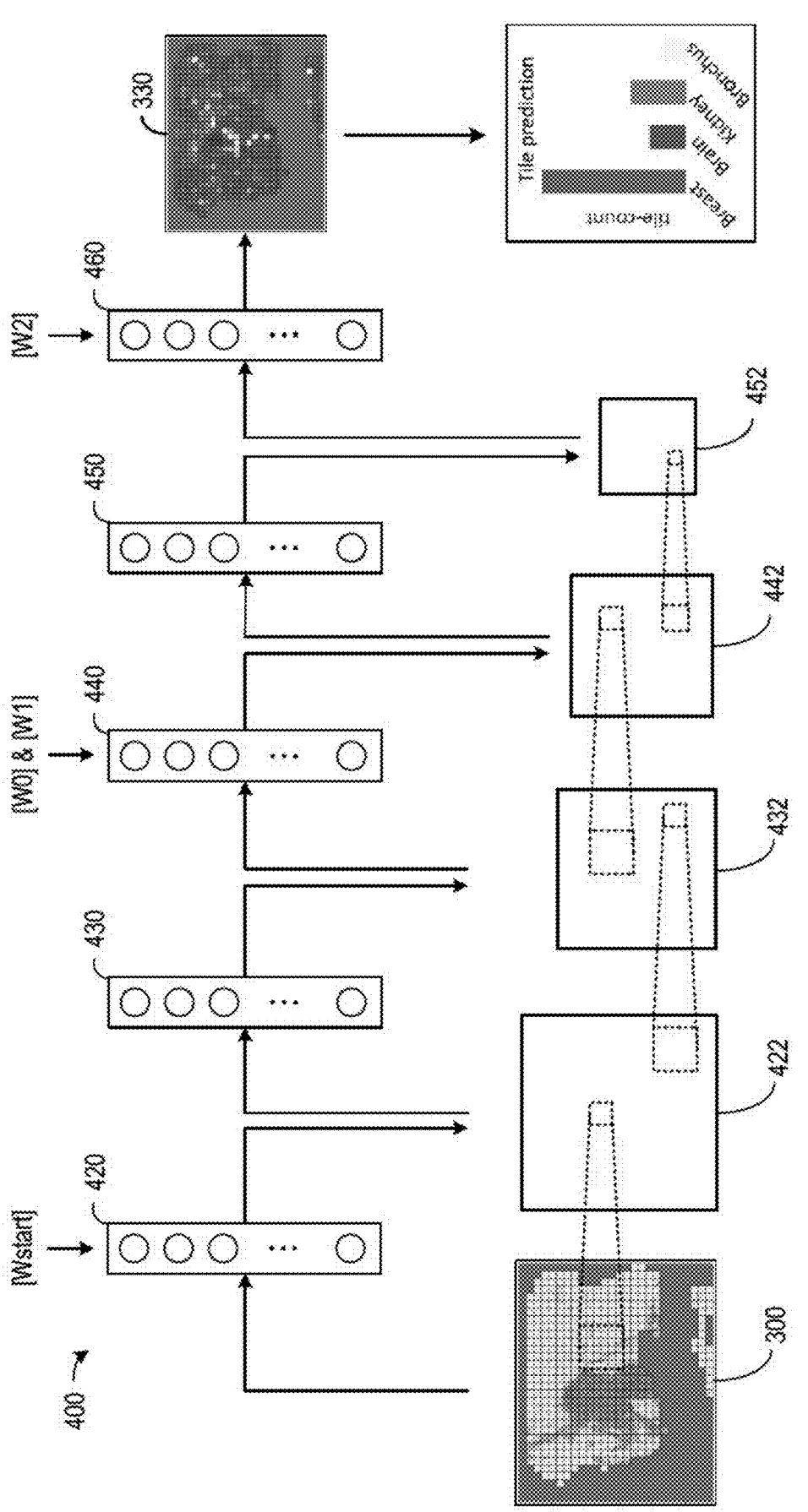

FIG. 4A and FIG. 4B illustrate examples of a convolutional neural network (CNN) 400 that can be part of prediction model 210. FIG. 4A illustrates a simplified version of CNN 400. As shown in FIG. 4A, CNN 400 includes at least an input layer 402, a middle layer 404, and an output layer 406. Input layer 402 and middle layer 404 together can perform the convolution operations to generate convolution outputs. Moreover, middle layer 406 and output layer 406 together can perform a classification operation to compute the probabilities of a tile being classified into each of candidate biological attributes, as a tile-level prediction output for the tile.

Specifically, input layer 402 can include a set of input nodes, such as input nodes 402a, 402b, 402c, 402d, 402e, and 402f. Each input node of input layer 402 can be assigned to receive a pixel value (e.g., p0, p1, p2, p3, p4, or p5) from a medical image, such as medical image 106, and scale the pixel based on a weight of a weight array [W1] as described in Equation 1 above. Weight array [W1] can be part of kernel 310 and can define the image features to be detected in the pixels for a particular type of biological attribute (e.g., a source organ type, an extraction method, and a protein expression).

In addition, middle layer 404 can include a set of middle nodes, including middle nodes 404a, 404b, and 404c. Each middle node can receive the scaled pixel values from a group of input nodes that overlap with kernel 310 of FIG. 3A. Each middle node can sum the scaled pixel values to generate a convolution output according to Equation 1. For example, middle node 404a can generate a convolution output c0 based on scaled pixel values p0, p1, p2, and p3, middle node 404b can generate a convolution output c1 based on scaled pixel values p1, p2, p3, and p4, whereas middle node 404c can generate a convolution output c2 based on scaled pixel values p2, p3, p4, and p5.

Each middle node can scale the convolution output with a set of weights defined in a weight array [W2]. Weight array [W2] can define a contribution of a convolution output to the tile-level prediction and can be specific for the type of biological attribute to be predicted. Output layer 406 include nodes including, for example, nodes 406a and 406b. Each node can output a probability of the tile being classified to have a particular candidate biological attribute. The number of nodes of output layer 406 can be given by the number of candidate biological attributes the tile can be classified to have. For example, in a case where the tile is to be classified into one of ten source organs, output layer 406 can have ten nodes. Each node of output layer 406 can receive a scaled convolution output from each node of middle layer 406, sum the scaled convolution outputs, and process the sum with an activation function to generate a probability of the tile having a particular biological attribute. For example, node 406a can output the probability of the tile being classified into a lung, whereas node 406b can output the probability of the tile being classified into a breast.

FIG. 4B illustrates additional details of CNN 400. As shown in FIG. 4B, CNN 400 may include four main operations: (1) convolution; (2) non-linear activation function (e.g., ReLU or softmax); (3) pooling or sub-sampling; and (4) classification.

As shown in FIG. 4B, medical image 300 may be processed by a first convolution network 420 using a first set of weight arrays (e.g., [Wstart] in FIG. 4B). As part of the convolution operation, blocks of pixels of medical image 300 can be multiplied with first weights array to generate a sum. Each sum is then processed by a non-linear activation function (e.g., Rectified Linear Unit (ReLU) and softmax) to generate a convolution output, and the convolution outputs can form a first output tensor 422. The first weights array can be used to, for example, extract certain basic features (e.g., edges) from medical image 300, and first output tensor 422 can represent a distribution of the basic features as a basic feature map. Output tensor (or feature map) 422 may be passed to a pooling layer 430, where first output tensor 422 may be subsampled or down-sampled by pooling layer 430 to generate a second output tensor 432.

Second output tensor 432 may be processed by a second convolution network 440 which can include input layer 402 and middle layer 404 of FIG. 4A using a second weights array (e.g., [W1] in FIG. 4A). The second weights array can be used to, for example, identify patterns of features for a particular biological attribute type, such as a type of organ from second output tensor 432. As part of the convolution operation, blocks of pixels of matrix 414 can be multiplied with the second weights array to generate a sum. Each sum is then processed by a non-linear activation function (e.g., ReLU or softmax) to generate a convolution output, and the convolution outputs can form a third output tensor 442. Third output tensor 442 (or feature map) from second convolution network 440 may represent a distribution of features representing a type of organ. Third output tensor 442 may be passed to a pooling layer 450 to be subsampled or down-sampled to generate a fourth output tensor 452.

Fourth output tensor 452 can then be passed through a fully-connected network 460, which can include a multi-layer perceptron (MLP), such as middle layer 404 and output layer 406 of FIG. 4A, to perform a classification operation. The classification output can include, for example, probabilities of a tile being classified into one of a lung or a breast, as described in FIG. 4A. Fully-connected layer 460 can also multiply fourth output tensor 452 with a third weights array (labeled [W2]), which can be associated with a particular biological attribute type, to generate sums, and the sums can also be processed by an activation function (e.g., ReLU or softmax) to generate array 330 of tile-level prediction outputs shown in FIG. 3C. From array 330, a slide-level prediction can then be made based on the tile-level prediction output having the maximum tile counts.

D. Training

Figure 5:
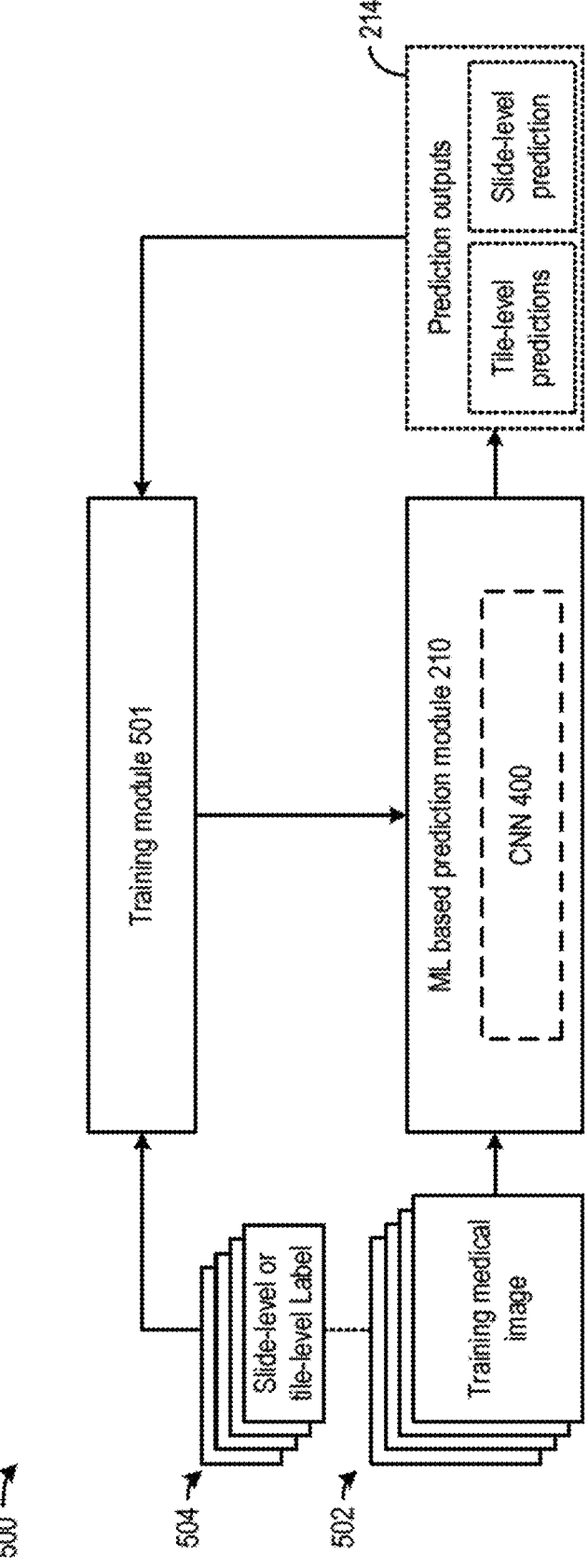
FIG. 5 illustrates an example training operation of medical data checker system of FIG. 2A-FIG. 4B, according to certain aspects of this disclosure.

Various parameters of prediction model 210, including weights W1, W2, and W3 of CNN 400 shown in FIG. 4B, can be trained based on a supervised training operation. FIG. 5 illustrates an example of a training operation 500 that can be performed by a training module 501. As part of training operation 500, prediction module 210, which includes CNN 400, can receive a set of training medical images 502 as inputs. Training medical images 502 can be associated with different biological attributes of a particular biological attribute type (e.g., different source organs, different extraction methods, or different protein types). Each training medical image can be associated with a label 504 indicating the biological attribute of the training medical image. Through the training operation, the weights can be adjusted to maximize the matching between the target prediction of features associated with the training medical images and the predicted biological attributes output by prediction module 210 for the training medical images. In addition, multiple sets of training medical images 502, with each set associated with a different type of label (e.g., organ type, extraction method, protein expression, gender, etc.)., can be used to train different sets of weights of the CNN 400 to predict different types of biological attributes.

The supervised training operation can be performed using various techniques. In some examples, each tile of a training medical image can be associated with a tile-level label 540 indicating the biological attribute of the tile (e.g., a source organ of the tissue imaged in the tile, a an extraction method of the tissue, or a protein expression). Training module 510 can implement a loss function that measure the differences between the label of each tile and the tile-level prediction (e.g., the biological attribute predicted with the highest probability). Training module 510 can adjust the weights to reduce/minimize the differences between the tile-level predictions of the tiles of the training medical images and the labels of the tiles.

In some examples, CNN 400 can be trained based on a cross-entropy loss function. Cross-entropy generally refers to a measure of the difference between two probability distributions for a given random variable or set of events. Entropy can refer to the number of bits required to transmit a randomly selected event from a probability distribution, whereas a cross-entropy calculates the number of bits required to represent or transmit an average event from one distribution compared to another distribution. The cross-entropy between a target distribution, P, and an approximation of the target distribution, Q, can be calculated using the probabilities of the events from P and Q, as follows:

$$H(P,Q) = -\Sigma_x P(x) \times \log(Q(x)) \tag{Equation 3}$$

In Equation 3, P(x) is the probability of the event x in P, whereas Q(x) is the probability of event x in Q.

Cross-entropy can be used as a loss function to optimize a machine learning model, such as CNN 400 operating as a classifier. As explained above, CNN 400 can compute, for each tile, a probability for each candidate tile-level prediction output. A cross-entropy loss function can be determined for that tile based on the expected probability of each candidate tile-level prediction output in the training data (e.g., based on a distribution of the known source organs of the specimens being observed in the tile) and the predicted probability output by CNN 400 for each candidate tile-level prediction output based on Equation 3. The goal of training operation 500 can be to minimize the cross-entropy loss function of Equation 3.

In some examples, the supervised training operation can be part of a multiple instance learning (MIL) where a weak slide-level label is applied to a bag of instances of a training medical image with each tile of the training medical image being an instance. Each medical image can be associated with a slide-level label 504, and training module 510 can adjust the weights to reduce/minimize the differences between the slide-level predictions for the training medical images and the weak labels of the training medical images. With a weakly supervised training operation, the labeling of the training medical images can be performed at the image level rather than at the tile/pixel level. Such arrangements can reduce the effort involved in labeling the medical images which, in turn, allows a large volume of labeled medical images to be made available to improve the training of CNN 400. Meanwhile with the weak-supervised training operation, the adjustment of the weights based on the differences between the slide-level predictions and the weak labels of the training medical images can be performed at a lower rate (e.g., a lower loss gradient) than the adjustment of the weights based on the differences between the tile-level predictions and the tile labels. The weak-supervision can be performed to account for the fact that different types of cells that may be present in a tissue, and that tissues of different organs may have the same type of cells as different types of cells (e.g., tumor cells) that distinguish different between different organs, which can lead to tiles of the same medical image being predicted to have different biological attributes.

E. Test Results

Table 1 below shows the biological attribute prediction accuracy and F1 score for tile-level prediction and slide-level prediction of medical images that capture specimen slides at 5× magnification and at 20× magnification. The prediction can be performed by CNN 400 trained as a classifier to determine the probability for each candidate biological attribute and output the biological attribute associated with the highest probability as the predicted biological attribute. The training can be performed based on minimizing a cross-entropy loss function, as described above. The biological attribute being predicted is the source organ of the tissue specimen captured in the specimen slides out of candidate source organs of brain, bronchus and lung, breast, ovary, soft tissues, liver and bile duct, pancreas, prostate gland, and thyroid gland. For slide-level prediction, the prediction accuracy is based on a ratio between a number of medical images for which the source organ is correctly predicted and the total number of medical images. For tile-level prediction, the prediction accuracy is based on a ratio between a number of tiles in the medical images for which the source organ is correctly predicted and the total number of tiles in the medical images. The F1 score is based on a number of true positives (TP), false positives (FP), and false negatives (FN), as follows:

$$F_1 = -\frac{TP}{TP + \frac{1}{2}(FP + FN)} \qquad \text{(Equation 3)}$$

TABLE 1

|  | Prediction accuracy | F1 score |
|---|---|---|
| 5× Tile-level prediction | 0.79 | 0.79 |
| 5× Slide-level prediction | 0.92 | 0.92 |
| 20× Tile-level prediction | 0.76 | 0.76 |
| 20× Slide-level prediction | 0.89 | 0.89 |

As shown in Table 1, the accuracy of biological attribute prediction is generally higher from images with a lower magnification (5×) than from images with a higher magnification (20×). This can be because with a lower magnification, a larger area of the tissue specimen can be observed in the medical image, which can provide more complete information of the specimen slide and improve the accuracy of the prediction. In addition, slide-level prediction is generally higher than tile-level prediction. This is because each tile only contains a very small piece of the tissue specimen, and many of the tiles of a medical image may not include relevant information to determine a specific biological attribute, or may produce noise information that can lead to the wrong attribute prediction. But due the aggregation of the tile-level prediction based on majority voting, such noise information can be removed and are less likely to lead to wrong slide-level prediction result. For example, assuming that a prediction of a source organ is to be made by choosing from two candidate source organ types. Even if just 51% of the tiles have correct tile-level prediction results, the slide-level prediction based on the majority of tile-level predictions (51%) will be correct despite the noise from the remaining 49% of the incorrect tile-level prediction results. Because of the capability of the majority voting scheme in removing the noise from incorrect tile-level prediction results, slide-level prediction results are generally more accurate than tile-level prediction results.

F. Prediction Based on Slide-Level Representation

Figure 6:
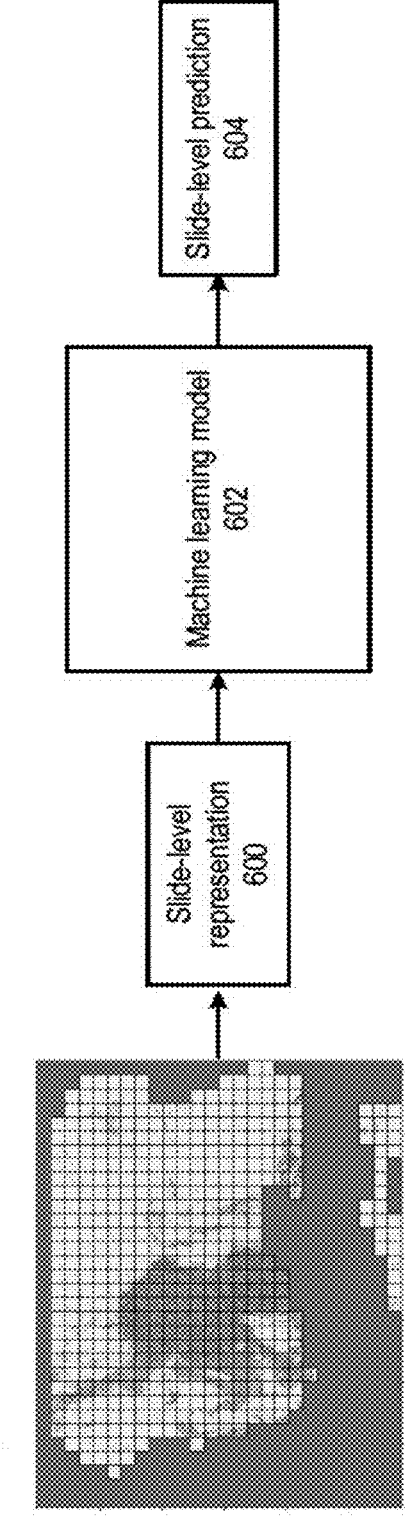
FIG. 6 illustrates example components of medical data checker system of FIG. 2A and FIG. 2B, according to certain aspects of this disclosure.

FIG. 6 illustrates another example of prediction operations of prediction module 210. As shown in FIG. 6, a slide-level representation 600 can be generated from medical image 300. Slide-level representation 600 can include a multi-dimensional vector with each dimension representing a feature, and the slide-level representation can include a set of feature values representing certain image features of the entire medical image 300 that can be used to predict a biological attribute of a particular biological attribute type (e.g., source organ, extraction method, or protein expression) of the medical image. In some examples, slide-level representation 600 can include feature values of multiple medical images of the same specimen slide obtained at different magnifications. With such arrangements, high resolution features of the specimen slide from a first medical image of a higher magnification, as well as more numerous features of the specimen slide from a second medical image of a lower magnification, can be included in the slide-level representation, such that the slide-level representation can provide a more complete yet detailed representation of various features (e.g., cell structures) of the specimen slide.

As to be describe below, slide-level representation 600 can be generated based on tile-level representation of the tiles of medical image 300. The tile-level representations can include an embedding vector that emphasizes relevant features that distinguish between tiles of different biological attributes and deemphasizes features that are common among the tiles or features that are not related to the biological attributes to be predicted. Slide-level representation 600 can be input to a machine learning model 602, which can be configured as a classifier, to generate a slide-level prediction 604 of a biological attribute (e.g., source organ, extraction method, and protein expression) of medical image 300. Components that generate slide-level representation 600, as well as machine learning model 602, can be part of prediction module 210 of FIG. 2A.

G. Generation of Slide-Level Representation

Figure 7A:
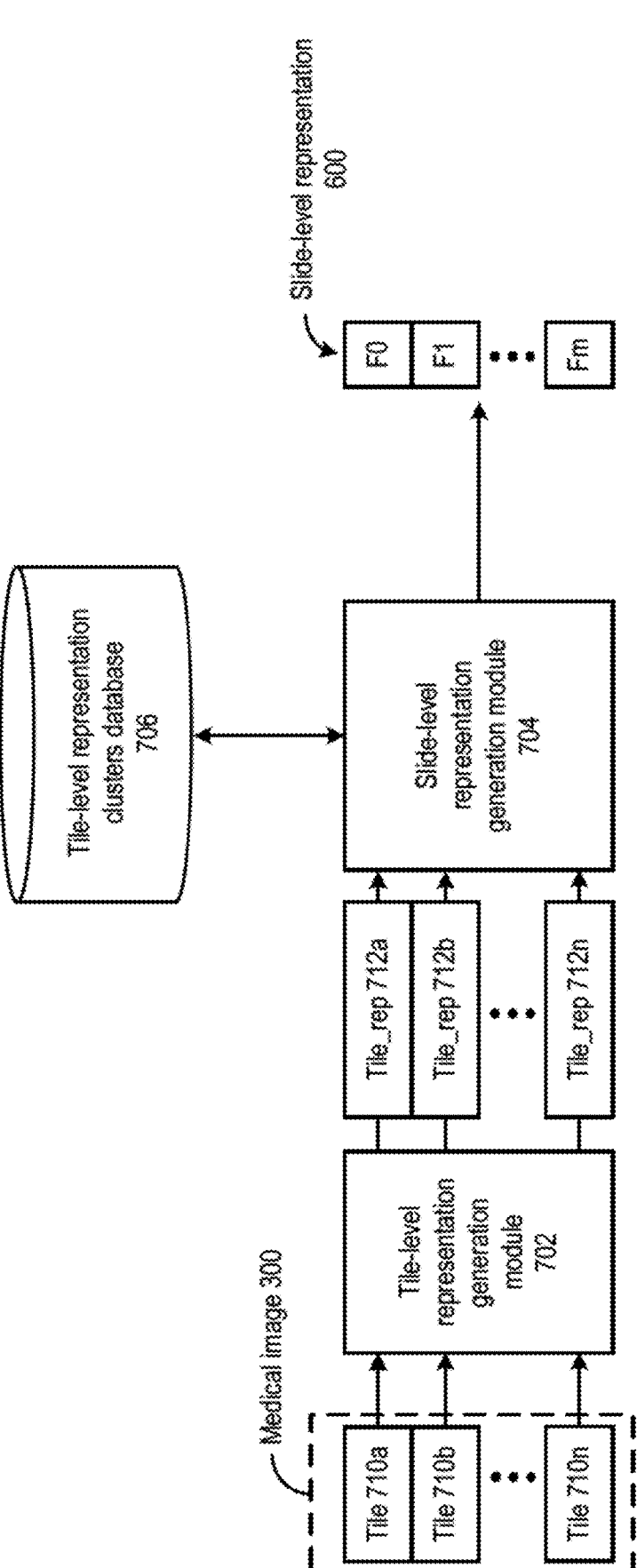
FIG. 7A, FIG. 7B, and FIG. 7C illustrate example components of medical data checker system of FIG. 2A and FIG. 2B and their operations, according to certain aspects of this disclosure.
Figure 7B:
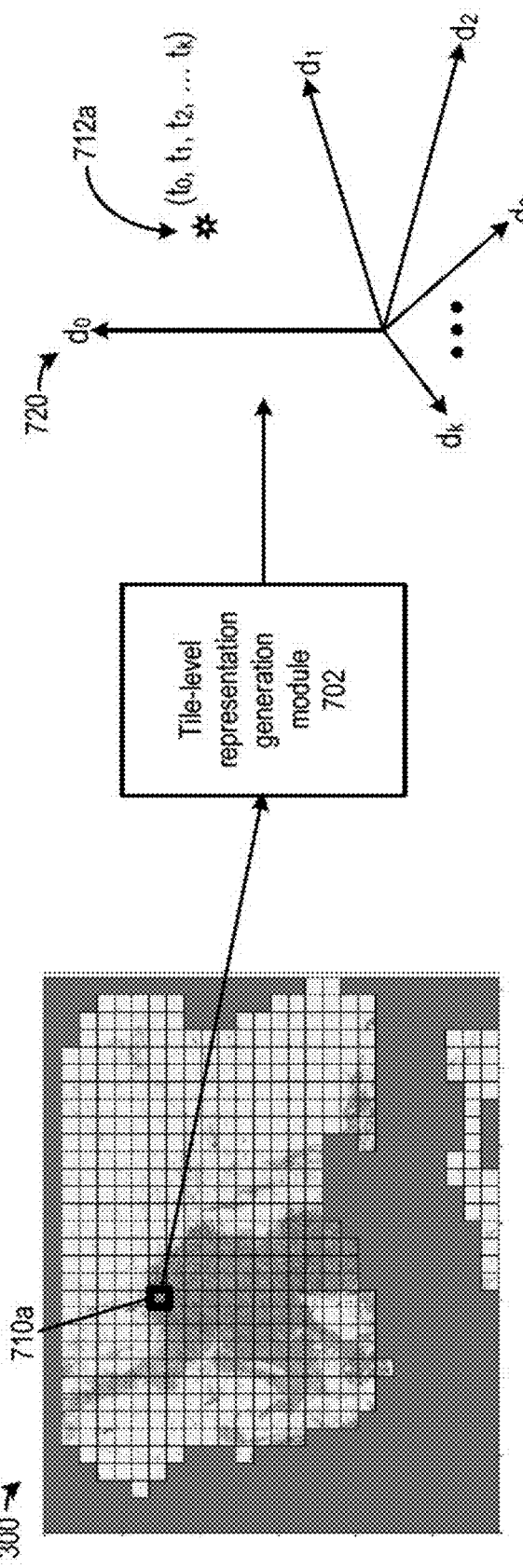
Figure 7C:
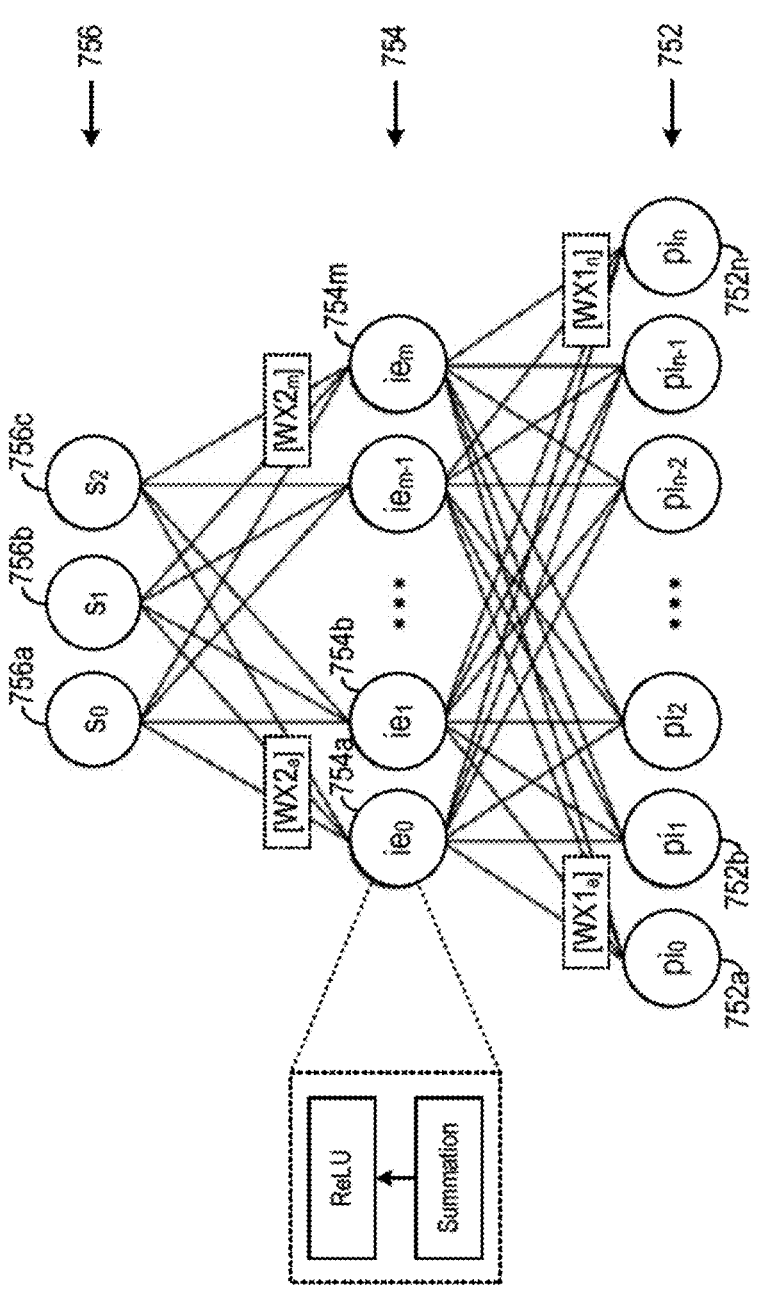

FIG. 7A, FIG. 7B, and FIG. 7C illustrate example techniques to generate slide-level representation. As shown in FIG. 7A, slide-level representation 600 can be generated from medical image 300 using a tile-level representation generation module 702, a slide-level representation generation module 704, and a reference tile-level representation clusters database 706, all of which can be part of prediction module 210. Medical image 300 can include a set of tiles such as, for example, tiles 710a, 710b, and 710n, with each tile including a block of pixel data. The pixel data of each tile can be input to tile-level representation generation module 702 which can generate a tile-level representation for each tile. For example, tile-level representation (labeled "tile_rep" in FIG. 7A) 712a is generated from tile 710a, tile-level representation 712b is generated from tile 710b, whereas tile-level representation 712n is generated from tile 710n.

The tile-level representations 712 can be input to slide-level representation generation module 704, which can compare tile-level representations 712 with clusters of reference tile-level representations from reference tile-level representation clusters database 706. The reference tile-level representations can be generated from the tiles of reference medical images using tile-level representation generation module 702. The reference medical images can be associated with different biological attributes of a particular biological attribute type (e.g., different source organs, different extraction methods, and different protein types). A distribution of the tiles of medical image 300 in the clusters of reference tiles can then be determined based on the comparison between tile-level representations 712 and the clusters of reference tile-level representations representing the clusters of reference tiles.

A set of feature values of slide-level representation 600, represented by F0, F1, . . . Fm in FIG. 7A, can represent the distribution of the tiles of medical image 300 in the clusters of reference tiles (represented by the clusters of reference tile-level representations). Each feature (e.g., one of F0, F1, and Fm) of slide-level representation 600 can represent a cluster of the reference tile-level representations, and a value of that feature can represent a count of the tiles of medical image 300 having the embedding vector in that cluster. The set of feature values of slide-level representation 600 can then be used as a signature of medical image 300 and can be input to machine learning model 602 to generate slide-level prediction 604 of FIG. 6.

In some examples, the tiles of multiple medical images, each of which is an image of the same specimen slide captured at a different magnification, can be processed by tile-level representation generation module 702 and slide-representation generation module 704 to generate the features of slide-level representation 600. In such examples, tile-level representation generation module 702 can have different sets of parameters (e.g., different sets of weights), with each set of parameters used to process tiles of a medical image of a particular magnification. Tile-level representation generation module 702 can then select a set of parameters based on the magnification the medical image. Moreover, slide-level representation clusters database 706 can store different sets of clusters of reference tile-level representations for different magnifications, and select a particular set of clusters of reference tile-level representations to determine a distribution of the tiles for a medical image of a particular magnification. Multiple distributions of tiles can then be determined for multiple images of different magnifications for a specimen slide can be determined, and multiple vectors representing the multiple distributions can be determined. Slide-level representation 600 can then be generated based on concatenating the multiple vectors.

i. Generation of Tile-Level Representations

FIG. 7B and FIG. 7C illustrate examples of generation of tile-level representations. As shown in FIG. 7B, the pixel data of a tile of medical image 300, such as tile 710a, can be input to tile-level representation module 702 to generate tile-level representation 712a, which can include multidimensional embedding vector. As shown in FIG. 7B, the multi-dimensional embedding vector can include a set of vector values t0, t1, t2, t3, . . . tk, each associated with, respectively, dimensions d0, d1, d2, d3, . . . dk, that defines an embedding space 720. The number of dimensions of embedding space 720 is generally fewer than the total number of pixels (e.g., 224×224 pixels) in a tile.

In some examples, the embedding vector can provide a mapping of discrete categorical variables into a vector of continuous numbers in an embedding space defined by, for example, dimensions d0-*dk* of FIG. 7B. The discrete categorical variable can represent, for example, the absence or presence of a feature of the tile. Some of the features may be relevant to distinguishing tiles of different biological attributes of a particular biological attribute type, while some of the features, such as common features shared by tiles of different biological attributes, can be less relevant or not relevant to distinguishing tiles of different biological attributes. Through the mapping, tiles having the same biological attribute can be represented by embedding vectors that are closer in the embedding space than tiles having different biological attributes. As such, each tile can be represented by an embedding vector that emphasizes relevant features that distinguish between tiles of different biological attributes of a particular biological attribute type and deemphasizes features that are common among the tiles or features that are not related to the biological attribute type to be predicted.

In some examples, tile-level representation generation module 702 can include a deep neural network which can be trained to generate embedding vectors that capture information of tiles that can distinguish tiles of different biological attributes. FIG. 7C illustrates an example of a deep neural network 750. As shown in FIG. 7C, deep neural network 750 can include an input layer 752, a hidden layer 754, and an output layer 756. Input layer 752 includes a plurality of nodes such as nodes 752a, 752b, and 752n. Hidden layer 754 includes a plurality of nodes such as nodes 754a, 754b, and 754m. Output layer 756 includes nodes such as node-pairs 756a, 756b, and 756c. Each node-pair of output layer 756 can correspond to a dimension of in embedding space 720 of FIG. 7B, which can have three dimensions in this example. Input layer 752, hidden layer 754, and output layer 756 can form a fully connected network, where each node hidden layer 754 is connected to each node of input layer 752 and each node of output layer 756 is connected to each node of hidden layer 754.

Each node of input layer 752 can receive a pixel value (e.g., pi0, pi1, or pin) of a tile, and scale it with a set of weights associated with the node. For example, node 752a is associated with a set of weights [WE1*a*], and node 352n is associated with a set of weights [WE1*n*]. Each node transmits the scaled values to all nodes of hidden layer 754. Each node of hidden layer 754, which can include one or multiple layers, receives a scaled value from each node of input layer 752 and sums the scaled values to generate an intermediate sum. The intermediate sum can be used to compute an embedding vector at output layer 756. For example, node 354a can compute an intermediate sum, sum354*a*, as follows:

$$\mathrm{Sum}_{754a} = \sum\nolimits_{j=0}^{n}(WE1_j \times p_j) \qquad \text{(Equation 4)}$$

In Equation 4, WE can represent a weight value of each set of weights (e.g., [WE1*a*] and [WE1*n*]) used by each node of input layer 752 to scale an input value inj, which can be either a SNP value (e.g., si0 or si1) or ancestral origin indicator c. The combination of ancestral origin indicator with the SNP values in computing intermediate sum can be equivalent to selecting different mapping functions for different ancestral origins.

Each node of hidden layer 754 also implements a non-linear activation function, such as ReLU or softmax, which defines the output of that node given the intermediate sum. The activation function can mimic the decision making of a biological neural network.

Each node of hidden layer 354 is associated with a second set of weights. For example, node 754a is associated with a set of encoder weights [WX2*a*] and node 754m is associated with a set of encoder weights [WX2*m*]. Each node can scale the output value of the activation function operation (e.g., ie0 for node 754a, ie1 for node 754b, and iem for node 754m) with the associated set of weights, based on Equation 3 above, to generate a set of scaled values and transmit the scaled values to nodes of output layer 756.

Each node of output layer 356 can correspond to a dimension in the embedding space. Each node of output layer 356 can receive the scaled intermediate values from hidden layer 354 and compute a value for a dimension of the embedding vector based on, for example, summing the scaled intermediate values. For example, node 756a can generate vector value s0, node 756b can generate vector value s1, whereas node 756c can generate vector value s2.

The weights [WX1] and [WX2] can be trained using a training operation similar to training operation 500 of FIG. 5 using supervised training techniques As part of the supervised training, tiles labelled with target embedding vectors can be used to train deep neural network 750. In some examples, self-supervised training techniques can be used to train a machine learning model to generate the embedding vectors. Different sets of weights [WX1] and [WX2] can be trained for different types of biological attributes. With such arrangements, the embedding vectors generated by deep neural network 750 can emphasize relevant features that distinguish between tiles of different biological attributes of a particular biological attribute type and deemphasizes features that are common among the tiles or features that are not related to the type of biological attribute to be predicted.

Besides deep neural network 750, other network topologies, such as CNN 400 of FIG. 4A (e.g., input layer 402 and middle layer 404) or a residual neural network (ResNET), can also be trained to generate embedding vectors for the tiles. Moreover, machine learning models trained using self-supervised learning techniques can also be used to generate embedding vectors for the tiles.

ii. Clusters of Reference Tile-Level Representations

To generate a slide-level representation (e.g., slide-level representation 600 of FIG. 6) for an input medical image, the tile-level representations of the input medical image can be compared with clusters of reference tile-level representations from reference tile-level representation clusters database 706. The reference tile-level representations can be generated as embedding vectors from the tiles of reference medical images using tile-level representation generation module 702. The same deep neural network model having the same sets of weights [WX1] and [WX2] can be used to generate both the embedding vectors of reference tile-level representations from the reference medical images, as well as the embedding vectors of tile-level representations from the input medical image. The embedding vectors of reference tile-level representations can then be clustered into clusters.

Figure 8A:
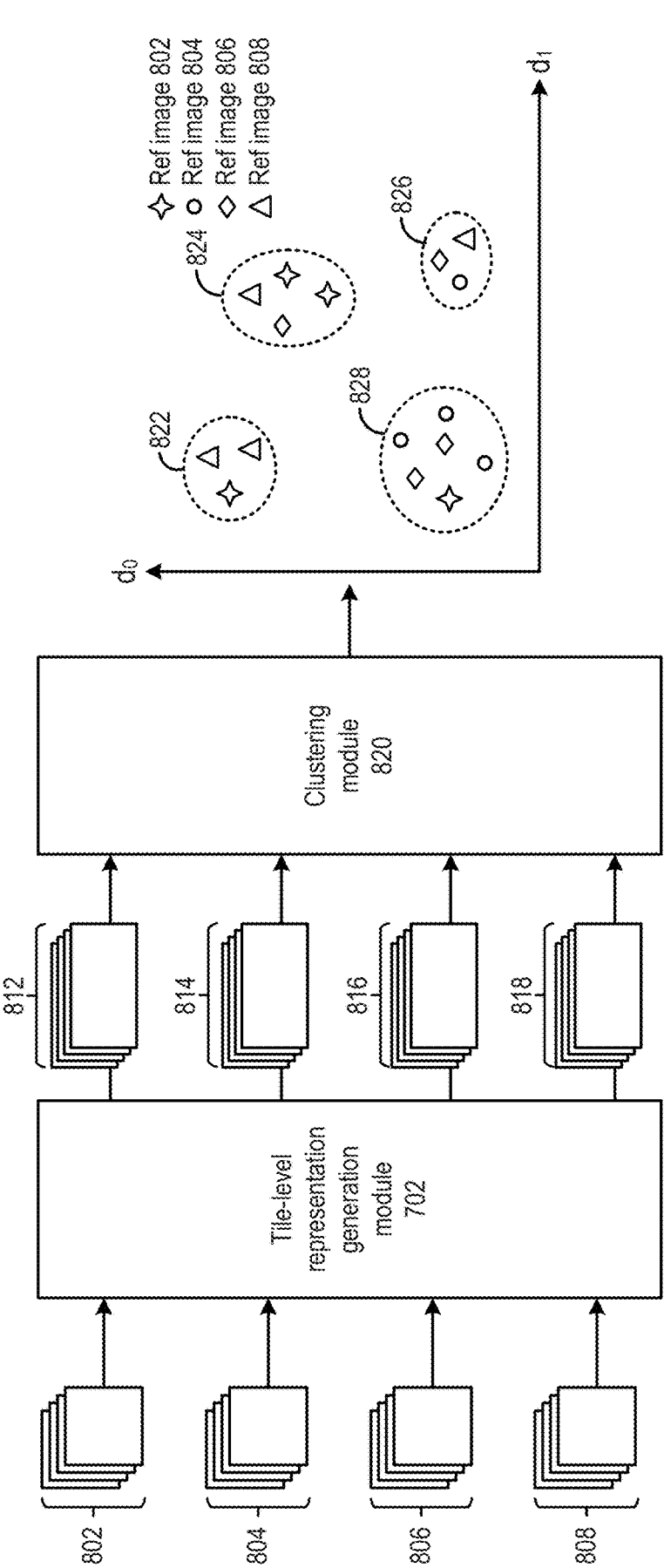

FIG. 8A illustrates an example of an operation to generate reference tile-level representations. As shown in FIG. 8A, tiles of reference medical images 802, 804, 806, and 808, each can be associated with different biological attributes of a particular biological attribute type (e.g., different source organs, different extraction methods, or different protein expressions) can be input to tile-level representation generation module 702 to generate a set of reference tile representations for each reference medical image. In the example of FIG. 8A, each reference medical image can have four tiles. Tile-level representation generation module 702 can generate a set of reference tile representations 812 for the tiles of reference medical image 802, a set of reference tile representations 814 for the tiles of reference medical image 804, a set of reference tile representations 816 for the tiles of reference medical image 806, and a set of reference tile representations 818 for the tiles of reference medical image 808. Each reference tile representation can include a multi-dimensional embedding vector. In the example shown in FIG. 8A, each tile representation can include a two-dimensional vector having vector values defined in a d0 dimension and a d1 dimension.

Sets of reference tile representations 812, 814, 816, and 818 can be input to a clustering module 820, which can cluster the embedding vectors of the reference tile representations into clusters. Clustering module 820 can cluster the reference tile representations using various clustering algorithms, such as k-means clustering. K-means clustering aims to partition the embedding vectors into k clusters with the goal of minimizing the variances among the embedding vectors clustered into each cluster. Other clustering techniques can also be used.

In the example of FIG. 8A, the embedding vectors of reference tile representations 812, 814, and 816 can be clustered into four clusters 822, 824, 826, and 828. In each cluster, each symbol represents a tile whose tile representation is in the cluster. For example, cluster 822 can include one tile from reference image 802 and two tiles from reference image 808. Cluster 824 can include two tiles from reference image 802, one tile from reference image 806, and one tile from reference image 808. Cluster 826 can include one tile from each of reference images 804, 806, and 808. Further, cluster 828 can include one tile from reference image 802, three tiles from reference image 804, and two tiles from reference image 806.

After the clustering operation by clustering module 820 completes, information of the clusters can be stored in tile-level representation clusters database 706. For example, referring to FIG. 8B, a table 830 can list, for each cluster, the vector values of the centroid of the cluster and the radius of the cluster, which can be stored in the database. In table 830 of FIG. 8B, cluster A can refer to cluster 822 and can have a centroid represented by vector values s0a and s1a along dimensions d0 and d1, and with a radius ra. Cluster B can refer to cluster 824 and can have a centroid represented by vector values s0b and s1b with a radius rb. Cluster C can refer to cluster 826 and can have a centroid represented by vector values s0c and s1c with a radius rc. Further, cluster D can refer to cluster 828 and can have a centroid represented by vector values s0d and s1d with a radius rd.

iii. Slide-Level Representation Generation Based on Comparison with Clusters of Reference Tile-Level Representations The clusters of the tile-level representations can be used to provide slide-level representations of images of different biological attributes. Specifically, different clusters of tile-level representations can represent distinguishing features in images of different biological attributes, whereas tile-level representations within the same cluster can represent common features in those images. A distribution of the tiles in the clusters of reference tiles can represent a distribution of distinguishing features and common features of a particular image. Given that different images of different biological attributes can have different distributions of distinguishing features and common features, a distribution of the tiles of an image in the clusters of reference tiles can be used as a signature to represent the image.

Accordingly, a slide-level representation can be generated for each reference image by slide-level representation generation module 704 based on the information of the clusters. Table 840 illustrates examples of slide-level representations 842, 844, 846, and 848 for, respectively, reference images 802, 804, 806, and 808. The slide-level representation can be a multi-dimensional vector. Referring to table 840, each cluster (e.g., one of clusters A, B, C, or D) can represent a feature/dimension in the slide-level representation, and a feature value of a feature in the slide-level representation can be based on a number of tiles of the reference image being in the cluster representing the feature or a ratio between the number of tiles of the reference medical image in the cluster and the total number of tiles of the reference medical image. As such, the slide-level representation can represent a distribution of the tiles, represented by the input tile-level representations, in the plurality of clusters of reference tiles.

For example, slide-level representation 842 can include a vector [1/4, 2/4, 0/4, 1/4] indicating that reference image 802 has one tile in cluster A, two tiles in cluster B, no tile in cluster C, and one tile in cluster D out of four tiles of the reference image. Moreover, slide-level representation 844 can include a vector [0/4, 0/4, 1/4, 3/4] indicating that reference image 804 has no tile in clusters A and B, one tile in cluster C, and three tiles in cluster D. Further, reference image 806 can be represented by a vector [0/4, 1/4, 1/4, 2/4] indicating that reference image 806 has no tile in cluster A, one tile in each of clusters B and C, and two tiles in cluster D. Reference image 808 can be represented by a vector [2/4, 1/4, 1/4, 0/4] indicating that reference image 808 has two tiles in cluster A, one tile in each of clusters B and C, and no tile in cluster D.

Figure 8C:
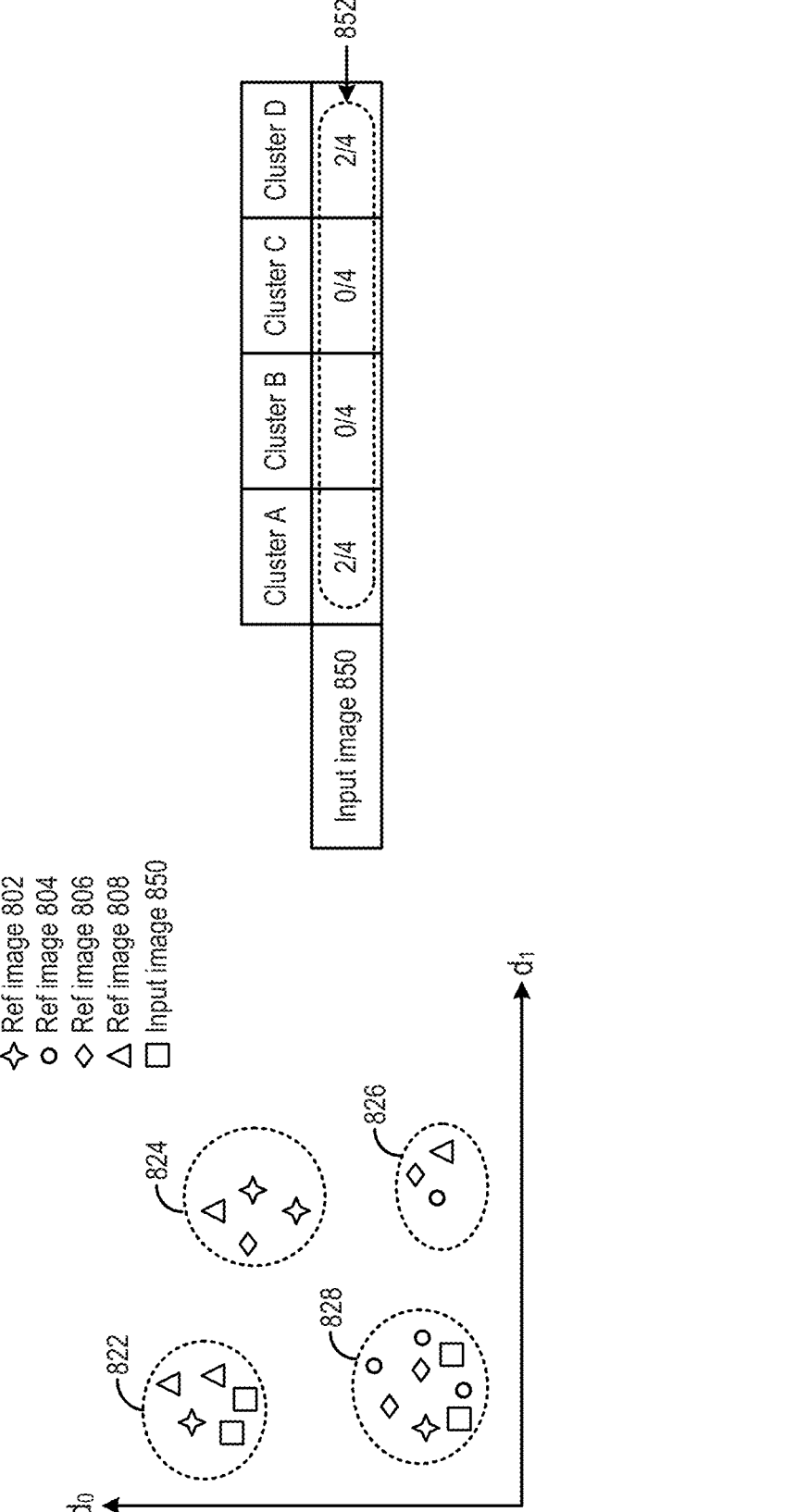

The slide-level representations of an input medical image can be generated based on comparing the tile-level representations of the input medical image and the clusters of the reference tile-level representations and determining a distribution of the tiles of the input medical image in the clusters. The comparison can be performed by slide-level representation generation module 704 based on table 830. Specifically, slide-level representation generation module 704 can determine a distance between the embedding vector of the tile-level representation of each tile of the input medical image against the centroids of each cluster and compare the distance against the radius of that cluster to determine whether the tile is in that cluster. Referring to FIG. 8C, for an input image 850 having four tiles, based on comparing the tile-level representations of the tiles of input image 850 with the clusters of reference tile-level representations, slide-level representation generation module 704 can determine that input image 850 has two tiles in cluster A, no tile in clusters B and C, and two tiles in cluster D and generate a slide-level representation 852 including a vector [2/4, 0/4, 0/4, 2/4].

Slide-level representations 842, 844, 846, and 848 of the reference images 802-808, as shown in table 840 of FIG. 8B, can be used to train machine learning model 602 of FIG. 6 to perform a prediction of a biological attribute from the slide-level representation of an input image, such as slide-level representation 852 of FIG. 8C. The use of slide-level representations to train a machine learning model to predict the biological attribute of an input medical image can further improve the accuracy of prediction. Specifically, each slide-level representation can represent an overall image, rather than a tile of the image. The reference images used to train machine learning model 602 can be labelled with the biological attributes associated with the images, and the parameters of machine learning model 602 can be adjusted at a higher rate based on mismatches between the labels and the slide-level prediction outputs compared with a case where the biological attributes are weak labels, as in FIG. 5. Compared with a weak-supervised training scheme in which the labels of the training images are weak labels to account for the different types of cells that may be present in a tissue and that tissues of different organs may have the same type of cell or cell structures, training machine learning model 602 using slide-level representations and labels of reference images can improve the accuracy of prediction by machine learning model 602.

In addition, slide-level representations generated based on the techniques described in FIG. 8A and FIG. 8B can include relevant information for distinguishing images of different biological attributes and can be used as signatures of medical images. Specifically, each tile-level representation can include an embedding vector that emphasizes relevant features that distinguish between tiles of different biological attributes and deemphasize features that are common among the tiles or features that are not related to the biological attributes to be predicted. Moreover, as explained above, a distribution of the tiles in the clusters of reference tiles can represent a distribution of distinguishing features and common features of a particular image. Given that different images of different biological attributes can have different distributions of distinguishing features and common features, a distribution of the tiles of an image in the clusters of reference tiles can be used as a signature to represent the image. All these can further improve the accuracy of prediction by machine learning model 602 trained using the slide-level representations.

H. Random Forest

Figure 9:
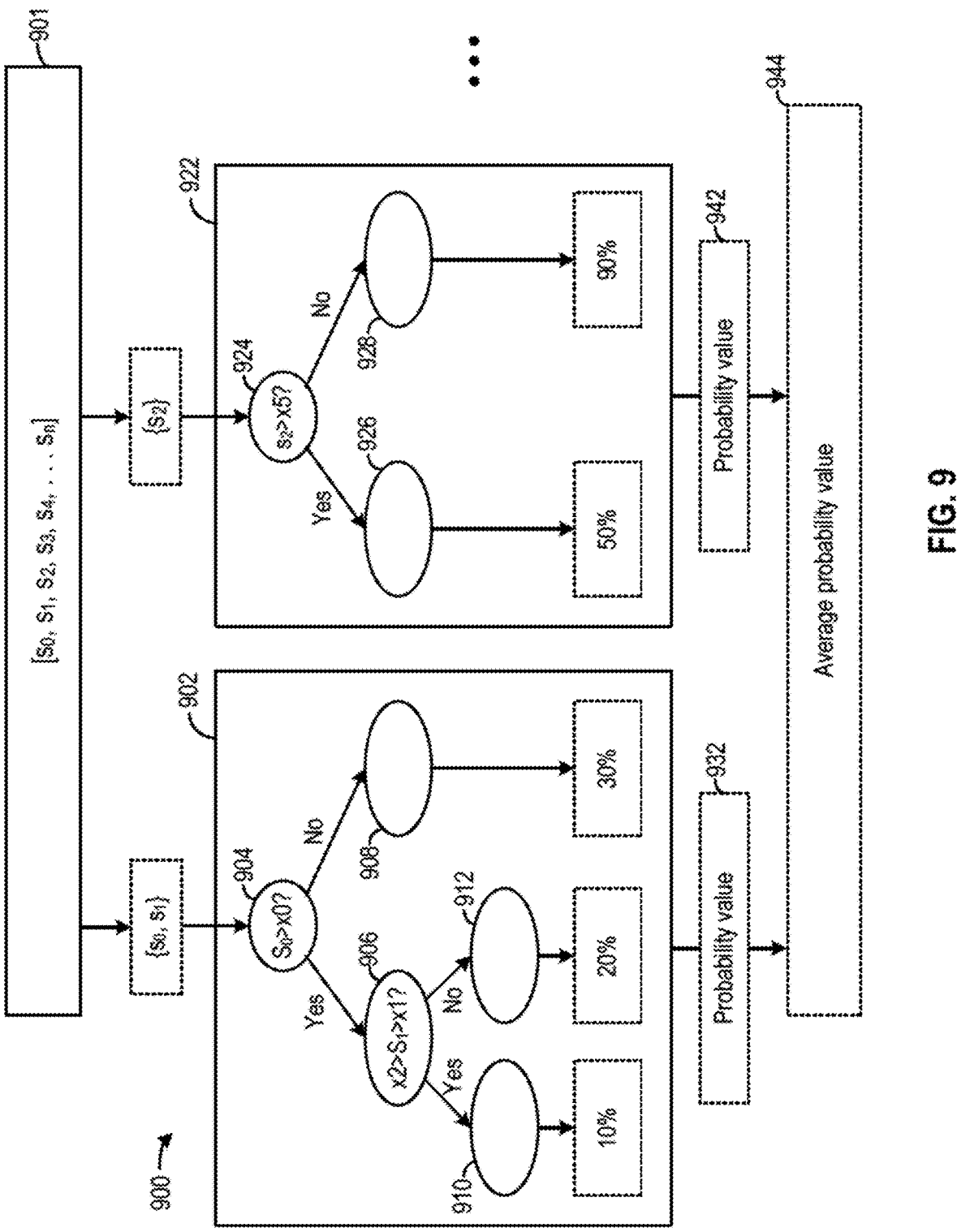
FIG. 9 illustrates an example component of medical data checker system of FIG. 2A and FIG. 2B, according to certain aspects of this disclosure.

Various types of machine learning model 602 can be trained using slide-level representations to predict a biological attribute of an input medical image. One example is a deep neural network trained as a classifier, such as CNN 400 and deep neural network 750. Another example is a decision tree, such as random forest, which can be trained using gradient boosting techniques. FIG. 9 illustrates an example of a random forest model 900 that can be used to implement machine learning model 602. As shown in FIG. 9, random forest model 900 can receive a vector 901 [s0, s1, s2, s3, s4, . . . sn] representing a slide-level representation. Random forest model can include a plurality of decision trees including, for example, decision trees 902 and 922. Each decision tree can include multiple nodes including a root node (e.g., root node 904 of decision tree 902, and root node 924 of decision tree 922), and child nodes (e.g., child nodes 906, 908, 910, and 912 of decision tree 902 and child nodes 926 and 928 of decision tree 922). Each parent node that has child nodes (e.g., nodes 904, 906, and 924) can be associated with pre-determined classification criteria to classify a patient into one of its child nodes. Child nodes that do not have child nodes are terminal nodes, which include nodes 910 and 912 (of decision tree 902) and nodes 926 and 928 (of decision tree 922), are each assigned a probability value for a particular candidate biological attribute. Each decision tree can classify the slide-level representation into one of the terminal nodes and outputs a probability value of the terminal node. For example, decision tree 902 can output a probability value 932 for a biological attribute indicating, for example, the medical image capturing a tissue specimen from a lung, whereas decision tree 922 can output a probability value 942 for the same biological attribute. The probability values from each decision tree can be averaged to generate an overall probability value 944 that the source organ for the tissue specimen captured in the medical image is a lung.

Each decision tree can be assigned to process different subsets of vector elements of the slide-level representation. For example, decision tree 902 can be assigned and trained to process vector elements {s0, s1}, decision tree 922 can be assigned and trained to process vector elements {s2}, while other decision trees can be assigned to process other subsets of data categories.

Each decision tree in a random forest model can be generated in a training process using a set of reference slide-level representations, as well as the known biological attributes of the set of reference medical images from which the reference slide-level representations are generated. In addition, the training process can determine the subsets of vector elements of the reference slide-level representations, the classification criteria at each parent node of the decision trees, as well as the probability value at each terminal node. Specifically, the training process can start with randomly assigning a subset of the vector elements of the reference slide-level representations to a root node of a decision tree, and different subsets of the vector elements can be assigned to the root nodes of different decision trees. The process of generating trees can be repeated until a target number of decision trees, which can be defined by hyper parameters of the training process, is reached. Moreover, in a bagging process, the root node of a decision tree can be assigned to a random set of samples of the reference slide-level representations to perform the training.

As part of the training process, the root node (and each parent node thereafter) can be split into child nodes in a recursive node-splitting process based on the random set of samples of the reference slide-level representations assigned to the root node. In the node-splitting process, a node assigned to process a set of reference slide-level representations can be split into two child nodes each assigned to process a subset of the reference slide-level representations based on thresholds for the subset of vector elements, with the subset of vector elements and their thresholds selected to, for example, maximize the difference in the numbers of reference slide-level representations of two different biological attributes. For example, referring to decision tree 902 during the training process, it can be determined that by dividing the random samples of reference slide-level representations assigned to decision tree 902 into two groups based on the vector element s0 and threshold x0, the difference between the number of reference slide-level representations classified to be lung tissue and the number of reference slide-level representations classified to be not a lung tissue can be maximized versus other classification criteria (e.g., based on vector element s1 or setting a different threshold for s0).

The process can then be repeated on the child nodes to generate additional child nodes until, for example, a threshold minimum number of deaths/non-survival patients is reached in a particular child node, which can then become a terminal node. For example, among the reference slide-level representations classified into terminal nodes 908, 910, and 912, the number of reference slide-level representations classified to be not a lung tissue reaches the threshold minimum number, therefore the root-splitting operation stops at those nodes. The probability value output at each of these terminal nodes can be represented by a percentage of the reference slide-level representations classified to be lung tissue of the total number of the random set of reference slide-level representations assigned to the decision tree.

I. Test Results

Figure 10:
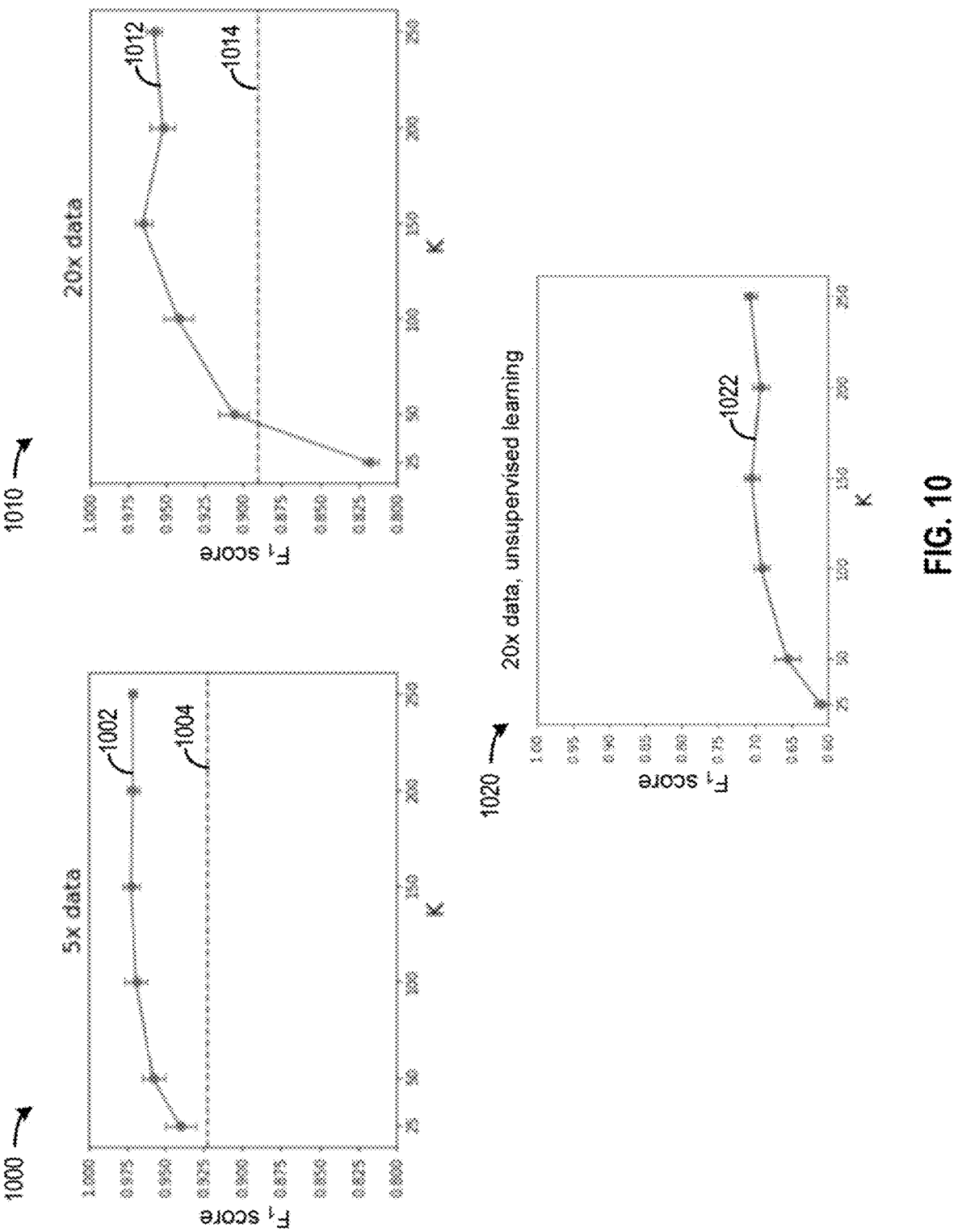
FIG. 10 illustrates examples of performance of a component of medical data checker system of FIG. 6-FIG. 9, according to certain aspects of this disclosure.

FIG. 10 illustrates examples of performances of machine learning model 602 trained to perform biological attribute prediction using slide-level representations, compared with biological attribute prediction based on aggregating tile-level predictions. In FIG. 10, charts 1000 and 1010 are performances of machine learning model 602 in making a prediction of a biological attribute based on slide-level representations generated from tile-level representations that are generated using a machine learning model trained using supervised learning techniques, such as deep neural network 750. Moreover, chart 1020 illustrates the performance of machine learning model 602 in making the prediction of the biological attribute based on slide-level representations generated from tile-level representations that are generated using a machine learning model trained using self-supervised learning techniques.

Referring to FIG. 10, chart 1000 includes a graph 1002 of a relationship between F1 scores and a number of clusters (K) for predicting a biological attribute from a set of medical images having a 5× magnification. The number of clusters K refers to the number of clusters of reference tile-level representations from which the slide-level representations are generated, as described in FIG. 8A-FIG. 8C. The number of clusters K also corresponds to the number of vector dimensions of the slide-level representations. For example, a K of 25 can indicate that the slide-level representation is a vector having 25 feature values for 25 dimensions. Chart 1000 also includes a graph 1004 of a F1 score of 0.925 from CNN 400 performing the biological attribute prediction on the same set of medical images with a 5× magnification based on aggregating tile-level predictions. The F1 score from CNN 400 is a constant and does not depend on the number of clusters.

Moreover, chart 1010 includes a graph 1012 of a relationship between F1 scores and a number of clusters (K) for predicting a biological attribute from a set of medical images having a 20× magnification, and a graph 1014 of a F1 score of 0.89 from CNN 400 performing the biological attribute prediction on the same set of medical images with a 20× magnification based on aggregating tile-level predictions. The F1 scores of both graphs 1002 and 1012 are generated based on the means of 5-fold cross-validation.

Further, chart 1020 includes a graph 1022 of a relationship between F1 scores and a number of clusters (K) for predicting a biological attribute from a set of medical images having a 20× magnification, based on slide-level representations generated from tile-level representations that are generated using a machine learning model trained using self-supervised learning techniques.

As shown in charts 1000, 1010, and 1020, the F1 scores improves with an increased number of clusters K which leads to an increased number of dimensions of the slide-level representations. This can be due to, for example, finer granularity in expressing the distinguishing features between medical images can be achieved with an increased number of clusters/dimension, which, in turn, can improve the prediction accuracy and the F1 scores. Moreover, the F1 scores achieved using machine learning model 602 with slide-level representations are in generally higher than the F1 scores achieved using CNN 400 and based on aggregation of tile-level predictions, especially with a high K number. Moreover, the F1 scores of prediction based on medical images of 5× magnification are generally higher than for medical images of 20× magnification, which is also consistent with Table 1 above. Lastly, comparing charts 1000, 1010, and 1020, the F1 scores of prediction based on slide-level representations generated from tile-level representations that are generated using a machine learning model trained using unsupervised learning techniques are generally lower compared with tile-level representations generated from machine learning models trained using supervised learning techniques, as supervised learning techniques are likely more effective in training a machine learning model to generate high quality embedding vectors that can differentiate tiles of different biological attributes.

J. Similarity Search

Figure 11A:
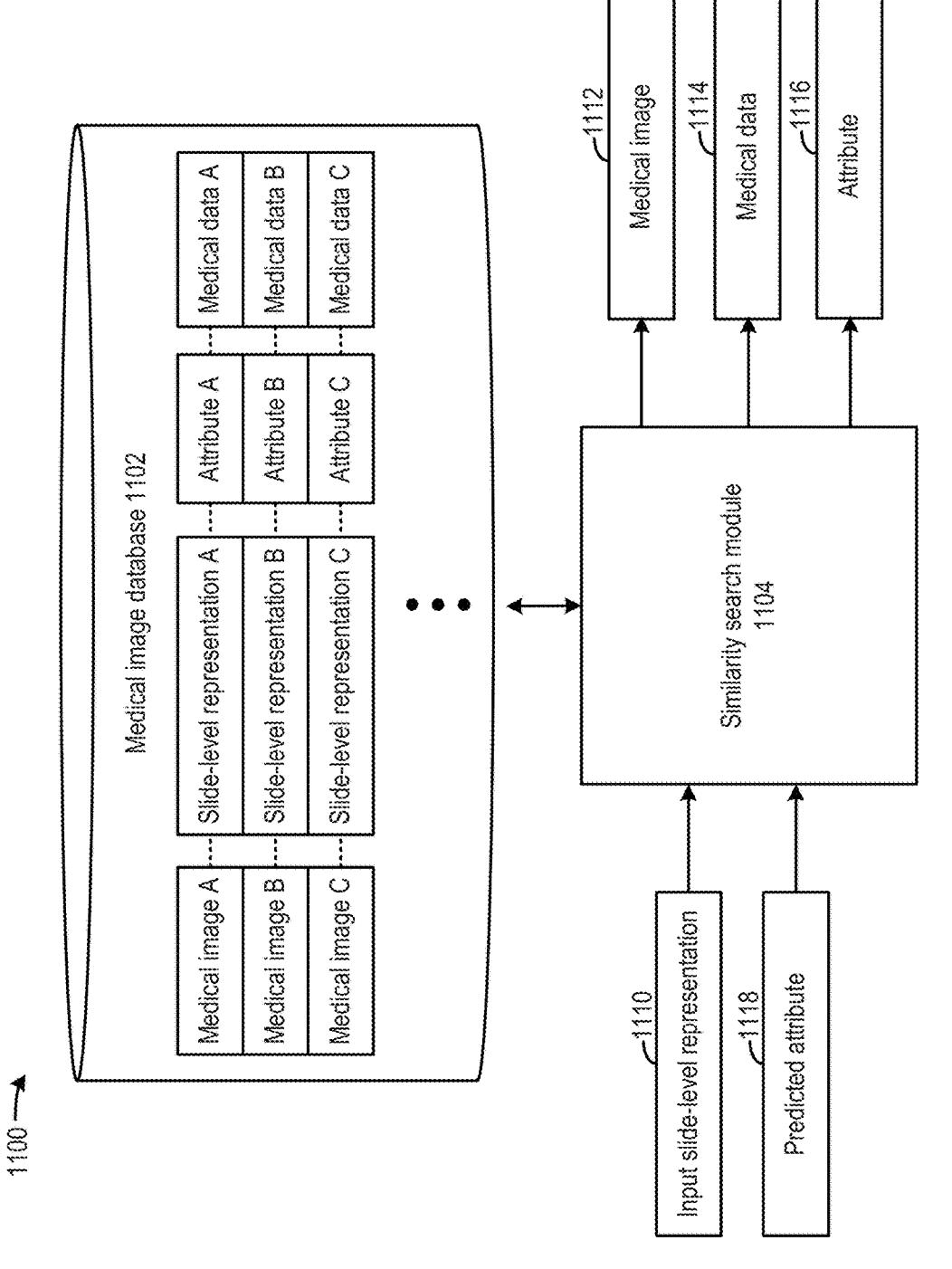
FIG. 11A and FIG. 11B illustrate a method of verifying multi-modal medical data, according to certain aspects of this disclosure.

In some examples, the slide-level representation of the input medical image can also be used to perform a similarity search for medical images that are similar to the input medical image. The medical images being searched can have the same biological attribute as the predicted biological attribute of the input medical image output by prediction module 210. FIG. 11A illustrates an example of a medical image search system 1100 that can be part of external to medical data checker system 200 of FIG. 2A. As shown in FIG. 11A, medical image search system 1100 can include a medical image database 1102 and a similar search module 1104. Medical image database 1102 can store a set of medical images (e.g., medical images A, B, and C) of specimen slides. Each medical image is associated with a slide representation (e.g., slide-level representations A, B, and C), one or more biological attributes (e.g., biological attributes A, B, and C), and medical data (e.g., medical data A, B, and C) of a subject from which the tissue specimen is extracted. In some examples, the medical data can be part of metadata of the medical image.

Specifically, the set of medical images in medical image database 1102 can include reference medical images used to generate the clusters of reference tile-level representations, which, in turn, are used to generate the slide-level representation of the input medical image, as described above. Moreover, the medical data can include, for example, a diagnosis result of the subject or treatment history of the subject. The slide-level representations in medical image database 1102 can be generated from the medical images using tile-level representation generation module 702. In addition, the one or more biological attributes of the medical images can include candidate biological attributes from which prediction module 210 is to make a prediction for an input medical image. In some examples, each medical image can be associated with a biological attribute of a biological attribute type, whereas in some other examples each medical image can be associated with multiple biological attributes of different biological attribute types.

Similarity search module 1104 can receive, as input, an input slide-level representation 1110 of an input medical image and perform a similarity search in medical image database 1102 for one or more slide-level representations that are similar to input slide-level representation 1110. Input slide-level representation 1110 can be generated by slide-level representation generation module 704. The similarity search can be based on, for example, submitting a query for vectors of slide-level representations that have the shortest distance (e.g., Euclidean distance) from the vector of input slide-level representation 1110. The similarity search can be configured to find, for example, the N closest slide-level representations.

Similarity search module 1104 can output data that are associated with the n closest slide-level representations, such as medical image 1112, medical data 1114 and one or more biological attributes 1116. For example, if similarity search module 1104 determines that slide-level representation A is the closest to input slide-level representation 1110, among other all slide-level representations in database 1102, similarity search module 1104 can retrieve medical image A as medical image 1112, medical data A as medical data 1114, and one or more biological attributes A as biological attribute 1116. In some examples, similarity search module 1104 can also receive predicted biological attribute 1118, which can be generated by machine learning model 602 from input slide-level representation 1110. Similarity search module 1104 can verify that the retrieved medical image has a matching biological attribute as predicted biological attribute 1118. For example, if predicted biological attribute 1118 indicates that input slide-level representation 1110 is for a specimen slide obtained from a lung, similarity search module 1104 can verify that biological attributes A of the retrieved medical image A also indicate a specimen slide obtained from a lung.

Medical image 1112 and medical data 1114 retrieved by similarity search module 1104 can support various applications. For example, biological attribute 1116 retrieved by similarity search module 1104 can be used to verify predicted biological attribute 1118 of the input medical image based on the fact that the slide-level representations of those medical images are similar to each other, and the images are likely to have the matching biological attribute. As another example, the multi-modal medical data, such as treatment history and diagnosis result of the subject of the retrieved medical image can also provide useful information used to support a clinical decision for the subject of the input medical image. For example, if the subject of retrieved medical image 1112 is diagnosed of a certain type of cancer, as shown in medical data 1114, similar diagnosis can be made of the subject of input slide-level representation 1110.

Figure 11B:
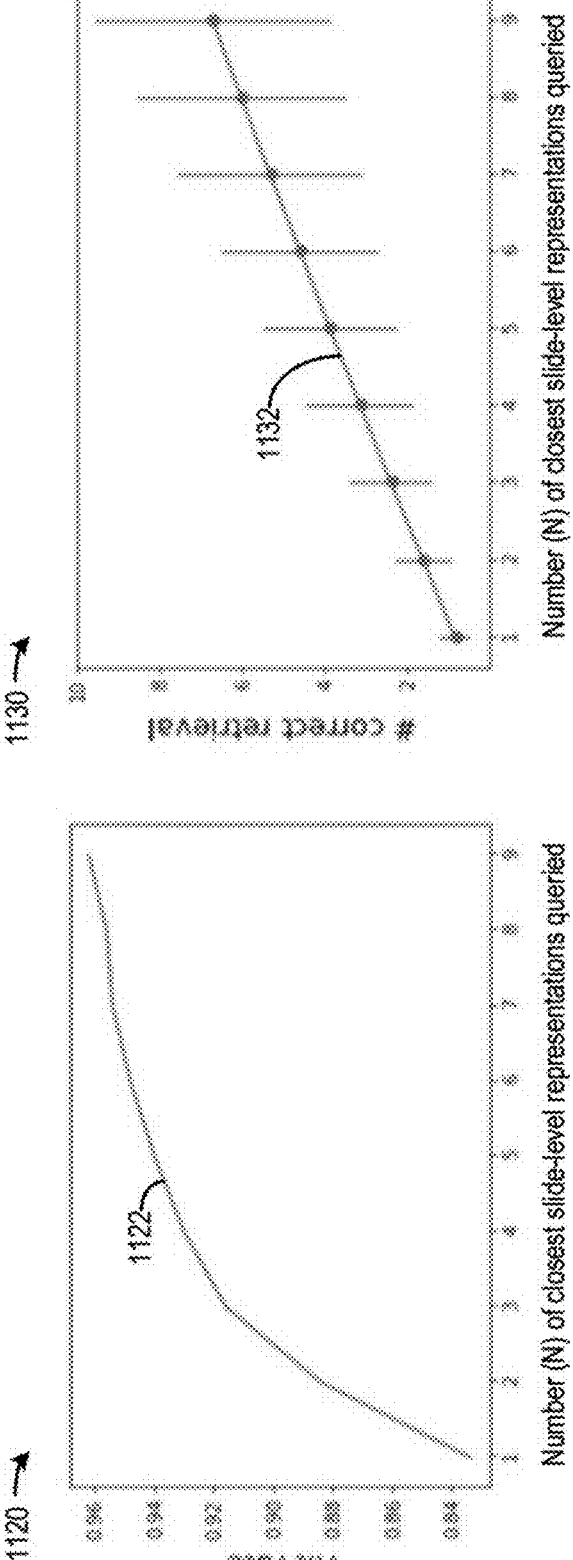

FIG. 11B illustrates examples of performance of similarity search module 1104. Chart 1120 plots a graph 1122 of a relationship between the number (N) of closest slide-level representations queried and a hit rate. The hit rate can refer to a ratio between a number of medical images correctly retrieved that have the same biological attribute (e.g., same source organ, same extraction method, same protein expression, etc.) as the medical image associated with input slide-level representation 1110, out of the N medical images associated with the N closest slide-level representations. Moreover, chart 1130 lots a graph 1132 of a relationship between the number (N) of closest slide-level representations queried and the number of medical images correctly retrieved. In both charts, it can be seen that as the number of closest slide-level representations queried increases, it is more likely to include a medical image having the same biological attribute as the input medical image, which can lead to a higher hit rate. The hit rate may reach a plateau as the number (N) of closest slide-level representations queried further increases, as the number of medical images fetched that do not have the correct attribute may also increase.

K. Diagnosis Prediction

Figure 12A:

In some examples, the slide-level representations can also be used to train a machine learning model (e.g., decision trees) to perform a prediction of a diagnosis of the subject. FIG. 12A illustrates an example of a diagnosis prediction module 1200 and its operation. Diagnosis prediction module 1200 may include a machine learning model, such as random forest model 900, that is trained using slide-level representations to generate probability values for different candidate diagnoses based on features of a specimen slide, and a diagnosis prediction 1202 associated with the highest probability can be output by diagnosis prediction module 1200. The diagnosis may include, for example, a type of tumor (e.g., a brain tumor, a liver tumor, etc.). The predicted diagnosis support various applications, such as a clinical decision of a treatment for the subject, to verify the diagnosis of the subject included in the multi-modal medical data of the subject, etc.

FIG. 12B illustrates examples of performance of diagnosis prediction module 1200. The diagnosis prediction shown in FIG. 12B is to classify between low grade glioma (LGB)

versus glioblastoma multiforme (GBM). In FIG. 12B, charts 1210 illustrates the performance of diagnosis prediction module 1200 in making a diagnosis prediction based on slide-level representations generated from tile-level representations that are generated using a machine learning model trained using supervised learning techniques, such as deep neural network 750. Moreover, chart 1220 illustrates the performance of diagnosis prediction module 1200 in making the diagnosis prediction based on slide-level representations generated from tile-level representations that are generated using a machine learning model trained using unsupervised learning techniques. The tile-level representations are generated from medical images of brain specimen slides obtained at 20× magnification. In both charts, the F1 scores with respect to the number of clusters K are plotted. As shown in both charts, the F1 scores are around 0.8 across a range of K from 25 to 250, indicating a reasonable high accuracy in classifying between LBM and GBM based on slide-level representations of images of brain specimen slides.

III. Method

Figure 13B:
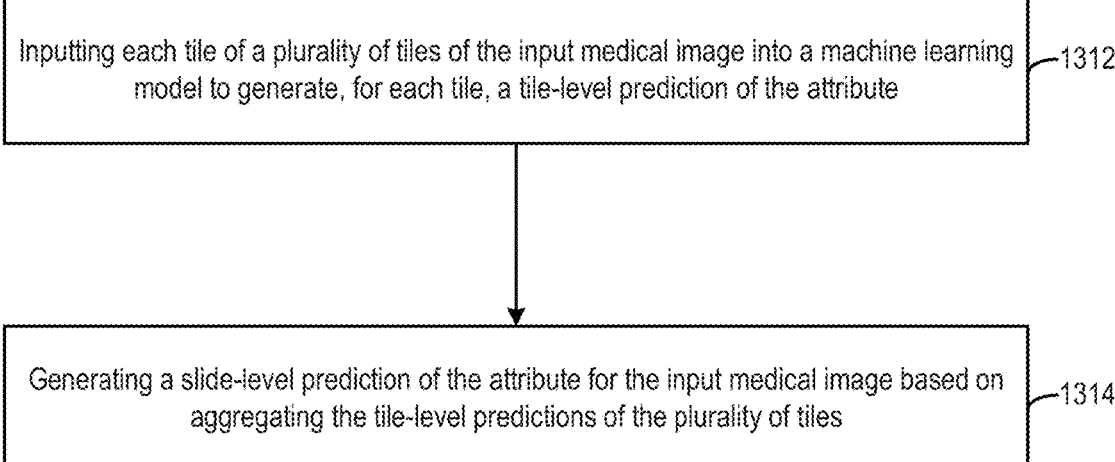

FIG. 13A and FIG. 13B illustrate a flowchart of an example method 1300 of verifying multi-modal medical data. Method 1300 can be implemented by, for example, medical data checker system 200 of FIG. 2A and FIG. 2B. The multi-modal medical data can belong to a cancer patient and can be verified prior to being provided to, for example, a medical collaboration application that hosts a tumor board meeting for the patient.

In step 1302, medical data checker system 200 can access multi-modal medical data of a subject, the multi-modal medical data comprising a medical image of a specimen slide, wherein a specimen in the specimen slide was collected from the subject. The multi-modal medical data can be accessed from one or more databases including, for example, an EMR (electronic medical record) system, a PACS (picture archiving and communication system), a Digital Pathology (DP) system, an LIS (laboratory information system), and a RIS (radiology information system). The multi-modal medical data can be those of a cancer patient and can include an medical image of a tissue specimen, as well as other modalities of medical data such as biography information of the patient and analytics data of the tissue specimen. The analytics data may include, for example, a site/location of the tumor, a type of the tissue specimen (e.g., biopsy, resection), and a mutation status of the patient. Different modalities of the multi-modal medical data can be received from different databases.

Referring to FIG. 2A, multi-modal medical data 102 may include biographical data 104, a medical image 106, analytics data 108, etc. Biographical data 104 can include various personal information of the patient, such as name, gender, age, and ethnicity. Medical images 106 can include images of a tissue specimen of the patient which has been stained to reveal various information. For example, in a case where the tissue specimen is stained with Hematoxylin and Eosin (H&E), medical images 106 can reveal cell structures of the tissue specimen which can include a tumor. Moreover, in a case where the tissue specimen is processed with immunostaining, medical images 106 can reveal the presence/absence of certain protein(s) in the tissue specimen, which can indicate a certain type of gene mutation. Analytics data 108 can various information related to medical images 106 such as its extraction method (e.g., biopsy versus resection), a site/location of a tumor (e.g., lung, brain, breast, ovary, or kidney) represented in medical images 106, and a status of gene mutation revealed in medical images 106.

Procedural history 110 can indicate a history of medical procedures received by the patient, including the procedures involved in the extraction of tissue specimens. For example, in a case where the patient receives a surgical resection procedure to remove the tissue specimen including a tumor, the resection procedure can be included as part of the treatment history of patient.

In step 1304, medical data checker system 200 can generate a prediction pertaining a biological attribute of the medical image based on the medical image. The biological attribute may be associated with a type, and for each biological attribute type, there can be a range of biological attributes from which a biological attribute can be predicted for the input medical image. For example, referring to FIG. 2B, the types of biological attributes can include a type of organ from which the tissue is extracted, and a range of biological attributes for the organ type can include, for example, brain, breast, bronchus and lung, or kidney. The types of biological attributes can also include a type of extraction method of the tissue specimen being observed in the image, and a range of biological attributes for extraction method type can include, for example, biopsy, or resection. Further, the types of biological attribute can also include a type of protein expression, and a range of biological attributes for a protein expression type can include, for example, an epidermal growth factor receptor (EGFR) protein, a KRAS protein, or tumor protein p53. The types of biological attributes can also include a type of tumor cell in the specimen.

In some examples, as shown in FIG. 3A-FIG. 5, a machine learning model including a convolutional neural network (CNN), which can include convolution layers to perform convolution operation and a fully-connected layer configured as a classifier, can be used to process the input medical image to perform the prediction. Referring back to FIG. 3A, the input medical image can include a set of tiles with each tile comprising a block of pixels.

FIG. 12B illustrates examples of sub-steps of step 1304. In sub-step 1312, medical data checker system 200 can input each tile of the set of tiles of the input medical image into a machine learning model, such as CNN 400, to generate, for each tile, a tile-level prediction of the feature. Specifically, referring to FIG. 3A-FIG. 4B, the CNN can perform convolution operations between a tile of the input medical image and a kernel to generate a convolution output for each tile. Based on the convolution output of the tile, the fully connected layer can compute a tile-level prediction output for each tile. The tile-level prediction output may include, for example, the probability of that tile being classified into one of a plurality of candidate biological attributes. For example, in a case where the biological attribute to be predicted is the source organ of a tissue specimen in the input medical image, the plurality of candidate biological attributes can include a plurality of candidate source organs, and one of the candidate source organs is to be selected as the source organ for the tissue specimen.

Moreover, in sub-step 1314, medical data checker system 200 can generate a slide-level prediction of the biological attribute for the input medical image based on aggregating the tile-level predictions of the plurality of tiles. In some examples, the aggregation can be based on a voting mechanism. Specifically, as described in FIG. 3C, tiles having a particular tile-level prediction output can be counted, and the tile counts for different tile-level prediction outputs can be obtained. A slide-level prediction can be made based on the tile-level prediction output having the maximum tile counts. For example, if the tile-level prediction output associated with a majority of the tiles indicate that the source organ is a lung, a slide-level prediction can be made that the source organ of the specimen slide of the input medical image is from the lung. In some examples, each tile can be assigned a scaling factor or a weight (e.g., between 0 and 1), and the tile count for each tile-level prediction output can be based on a sum of the scaling factors of the tiles having that tile-level prediction output. The scaling factor of a tile can reflect, for example, a confidence level of the tile-level prediction of the tile, and a degree of relevance of the tile-level prediction of the tile. The confidence level can be based on the probability of the tile having a particular biological attribute as indicated by the tile-level prediction output with a higher probability lead to a higher confidence level and vice versa. Moreover, the degree of relevance can be based on, for example, a location of the tile within the medical image or a distance of the tile from the expected locations of tissue/tumor cells that can identify the source organ.

In step 1306, medical data checker system 200 can determine a degree of consistency between the biological attribute of the input medical image and other modalities of the medical data. For example, determinations can be made about whether the predicted type of organ is consistent with the tumor site/location indicated in the medical data, whether the predicted extraction method is consistent with the tissue specimen (e.g., biopsy versus resection samples) shown in the medical image, whether the predicted mutation status is consistent with the mutation status indicated in the medical data, etc.

In step 1308, medical data checker system 200 can output, based on the degree of consistency, an indication of whether the multi-modal medical data contain inconsistency. Specifically, if inconsistency is detected, an indication of a potential misidentification error (e.g., incorrect name listed in the biographic data, the tissue specimen being swapped with another patient, or the analytics data being swapped with those of another patient) can be output in the medical application to warn a user of the medical application (e.g., a collaboration application, such as a tumor board application) that the multi-modal medical data contain potential inconsistencies.

FIG. 14 illustrates an example of a flowchart of an example method 1400 of performing a prediction of a biological attribute of a medical image. The biological attribute may include, for example, a type of organ from which the tissue is extracted, a type of extraction method, a type of protein expression, a type of tumor cell in the specimen, etc. Method 1400 can be implemented by a system comprising, for example, medical data checker system 200 of FIG. 2A and FIG. 2B, which can include machine learning model 602 of FIG. 6, tile-level representation generation module 702 and slide-level representation generation module 704. Method 1400 can also be implemented by similarity search module 1104 of FIG. 11A. In some examples, part of method 1400 can be part of step 1204 of FIG. 12A.

In step 1402, the system can access a medical image of a specimen slide, wherein a specimen in the specimen slide was collected from a subject, the medical image being part of multi-modal medical data of the subject. As described above, the multi-modal medical data can be accessed from one or more databases including, for example, an EMR (electronic medical record) system, a PACS (picture archiving and communication system), a Digital Pathology (DP) system, an LIS (laboratory information system), and a RIS (radiology information system). The multi-modal medical data can be those of a cancer patient and can include an medical image of a tissue specimen, as well as other modalities of medical data such as biography information of the patient and analytics data of the tissue specimen. The analytics data may include, for example, a site/location of the tumor, a type of the tissue specimen (e.g., biopsy, resection), and a mutation status of the patient. Different modalities of the multi-modal medical data can be received from different databases.

In step 1404, the system can define a set of tiles, wherein each of the set of tiles includes a different portion of the medical image. Each tile can include a block of pixels.

In step 1406, the system can generate, for each tile of the set of tiles, a tile-level representation of the tile.

Specifically, the tile-level representation can be generated using a first machine learning model, which can be part of tile-level representation generation module 702 and can include, for example, deep neural network 750. The tile-level representation can include an embedding generated based on inputting pixels of a tile into a fully-connected neural network. The embedding can be a multi-dimensional vector that emphasizes relevant features that distinguish between tiles of different biological attributes and deemphasizes features that are common among the tiles or features that are not related to the biological attributes to be predicted. Deep neural network 750 can be trained to generate embedding vectors for the tiles such that tiles having the same biological attribute are represented by embedding vectors that are closer in the embedding space than those tiles having different biological attributes. The training can be based on, for example, supervised training techniques, unsupervised training techniques, etc. As such, each tile can be represented by an embedding vector that emphasizes relevant features that distinguish between tiles of different biological attributes and deemphasizes features that are common among the tiles or features that are not related to the biological attributes to be predicted.

In step 1408, the system can assign, for each tile of the set of tiles, the tile to a particular cluster of a set of clusters based on the tile-level representation of the tile.

Specifically, referring to FIG. 8A, reference tile-level representations, which can include embedding vectors, can be generated from tiles of reference medical images of different biological attributes of the same biological attribute type using deep neural network 750. The reference tile-level representations can be clustered into multiple clusters based on various clustering algorithms, such as k-means clustering. After the clustering operation by clustering module 820 completes, information of the clusters can be stored in tile-level representation clusters database 706. For example, referring to FIG. 8B, table 830 can list, for each cluster, the vector values of the centroid of the cluster and the radius of the cluster, which can be stored in the database. Slide-level representation generation module 704 can then obtain table 830 from tile-level representation clusters database 706.

The assignment can be based on a relationship between the plurality of input tile-level representations and the clusters of reference tile-level representations. The assignment can be performed by slide-level representation generation module 704 based on table 830. Specifically, slide-level representation generation module 704 can determine a distance between the embedding vector of the tile-level representation of each tile of the input medical image against the centroids of each cluster and compare the distance against the radius of that cluster to determine whether the tile is in that cluster.

In step 1410, the system can determine a distribution of the cluster assignments across the set of clusters based on the tile assignments. The system can then generate the slide-level representation of the medical image based on the distribution, in step 1412.

Specifically, referring to FIG. 8C, slide-level representation generation module 704 can determine a distribution of the tiles of the input medical image in the clusters. A slide-level representation generation including a multi-dimensional vector can then be generated, where each dimension of the vector can be represented by a cluster of the clusters of tile-level representations and the value of each dimension of the vector can be based on a number of tiles of the input medical image in the cluster representing the dimension. In some examples, the value of a dimension can be based on a fraction or a decimal number representing a ratio between the number of tiles in the cluster and the total number of tiles of the input medical image.

In some examples, the slide-level representation can be generated based on multiple distribution of tiles in different clusters of tiles, with each distribution of tiles based on tiles from a medical image of a particular magnification of the same specimen slide.

In step 1414, the system can generate a prediction pertaining to the medical image based on the slide-level representation.

In some examples, the slide-level representation to a second machine learning model to generate a slide-level prediction of the biological attribute for the input medical image, as part of step 1304 of FIG. 13. In some examples, the second machine learning model can include gradient-boosted decision trees, such as random forest model 900 of FIG. 9.

In some examples, referring to FIG. 11A, the slide-level representation of the medical image can also be used to perform a similarity search for medical images that are similar to the input medical image. The medical images being searched can include reference medical images used to generate the clusters of reference tile-level representations which, in turn, are used to generate the slide-level representation of the input medical image, as described above, as well as other medical images. These medical images, as well as their slide-level representations, can be stored in a database. The medical images can also be associated with the medical data (e.g., diagnosis results and treatment history) of the subjects in the database. A similarity search can be performed based on finding vectors of slide-level representations that are within a certain distance (e.g., Euclidean distance) from the vector of the slide-level representation of the input medical image to retrieve medical images having similar slide-level representations as the input medical image, as well as the medical data associated with the medical images.

The medical images and medical data obtained from the similarity search can support various applications. For example, the biological attributes of the medical images can be used to verify the predicted biological attribute of the input medical image, based on the fact that the slide-level representations of those medical images are similar to each other and the images are likely to have the same biological attribute. As another example, the multi-modal medical data, such as treatment history, of the subjects of those medical images can also provide useful information used to support a clinical decision for the subject of the input medical image. In some examples, referring to FIG. 12A, the slide-level representation can be used to perform a diagnosis prediction (e.g., a severity of tumor, a type of tumor, etc.), which can be used to, for example, verify other modalities of medical data, to guide a treatment decision, etc.

IV. Computer System

Figure 15:
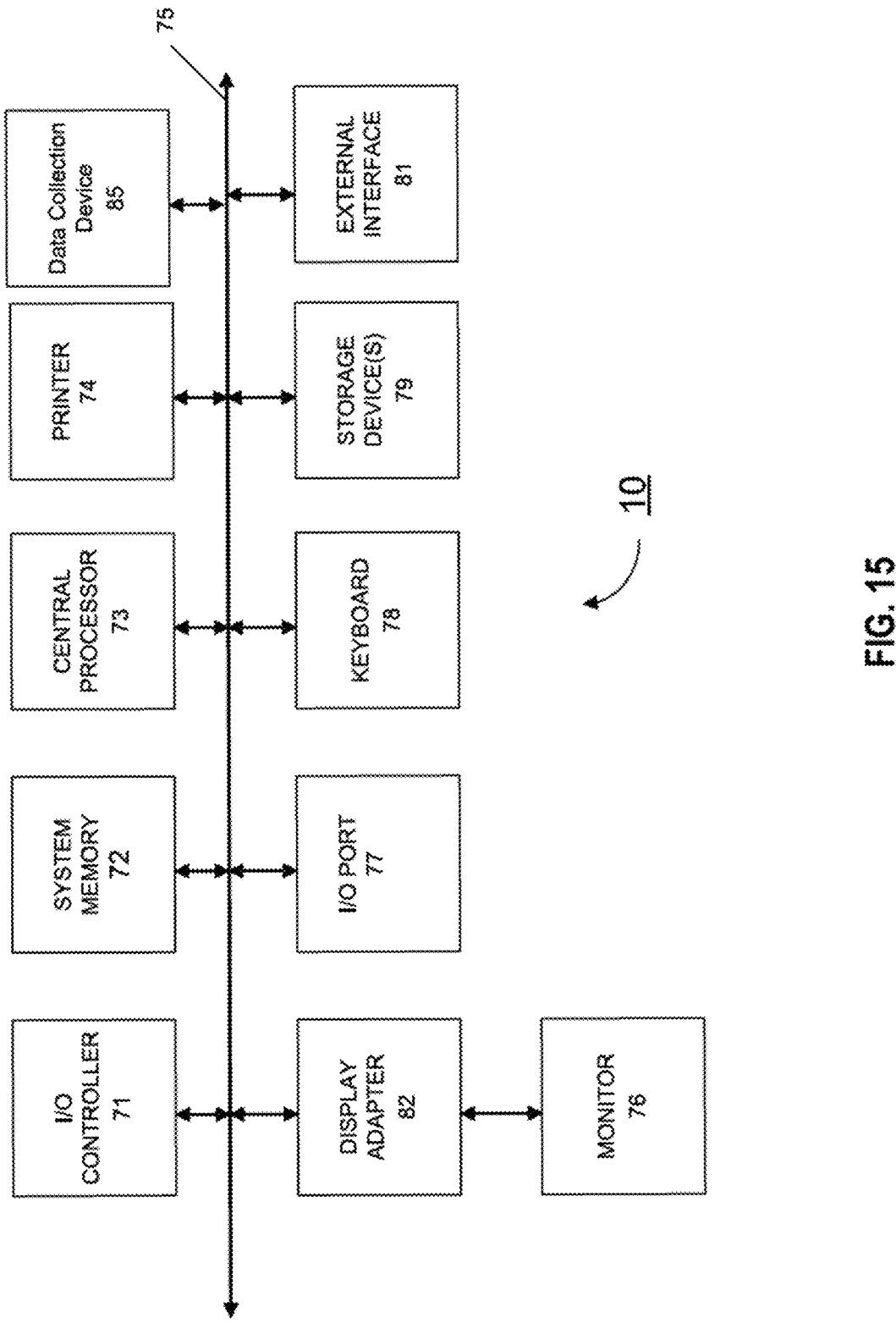
FIG. 15 illustrates an example computer system that may be utilized to implement techniques disclosed herein.

Any of the computer systems mentioned herein may utilize any suitable number of subsystems. Examples of such subsystems are shown in FIG. 15 in computer system 10, which can implement medical data checker system 200. In some embodiments, a computer system includes a single computer apparatus, where the subsystems can be the components of the computer apparatus. In other embodiments, a computer system can include multiple computer apparatuses, each being a subsystem with internal components. A computer system can include desktop and laptop computers, tablets, mobile phones and other mobile devices. In some embodiments, a cloud infrastructure (e.g., Amazon Web Services), a graphical processing unit (GPU), etc., can be used to implement the disclosed techniques.

The subsystems shown in FIG. 15 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet or Wi-Fi) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer-readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer-readable medium for storage and/or transmission. A suitable non-transitory computer-readable medium can include random-access memory (RAM), a read-only memory (ROM), a magnetic medium such as a hard-drive or a floppy disk, an optical medium such as a compact disk (CD) or DVD (digital versatile disk), flash memory, and the like. The computer-readable medium may be any combination of such storage or transmission devices.

Such programs may also be encoded and transmitted using carrier signals adapted for transmission via wired, optical, and/or wireless networks conforming to a variety of protocols, including the Internet. As such, a computer-readable medium may be created using a data signal encoded with such programs. Computer-readable media encoded with the program code may be packaged with a compatible device or provided separately from other devices (e.g., via Internet download). Any such computer-readable medium may reside on or within a single computer product (e.g. a hard drive, a CD, or an entire computer system) and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A computer implemented method for verifying the consistency of electronic medical records, the method comprising:

accessing electronic multi-modal medical data records of a patient, the multi-modal medical data comprising a medical image of a specimen slide;

generating a prediction pertaining to a biological attribute of the specimen based on the medical image;

determining a degree of consistency between the prediction and other modalities of the multi-modal medical data of the patient; and outputting, based on the degree of consistency, an indication of whether the electronic multi-modal medical data records contain inconsistency.

2. The method of claim 1, wherein the biological attribute is associated with one or more biological attribute types, the one or more biological attribute types comprising at least one of: a source organ of the specimen, an extraction method of the specimen, a protein expression of the specimen, or a type of tumor cell in the specimen.

3. The method of claim 1 further comprising:

defining a set of tiles, wherein each of the set of tiles includes a different portion of the medical image; and generating, for each tile of the set of tiles, a tile-level prediction pertaining to a biological attribute of the tile, wherein the prediction pertaining to the biological attribute of the specimen is generated based on aggregating the tile-level predictions of the set of tiles.

4. The method of claim 3, wherein the tile-level predictions of the set of tiles comprise tile-level predictions of a first biological attribute for a first subset of the set of tiles and a second biological attribute for a second subset of the set of tiles; and wherein generating the prediction pertaining to the biological attribute of the specimen based on aggregating the tile-level predictions comprises:

determining a first count for the first subset of the set of tiles associated with the first biological attribute;

determining a second count for the second subset of the set of tiles attributed with the second biological attribute, the second count based on a count of the tiles in the second subset of the set of tiles and/or a scaling factor for one or more of the second subset of tiles, the scaling factor based on at least one of: a confidence level or a degree of relevance of the tile-level prediction of the second biological attribute for the tile; and selecting the first biological attribute as the biological attribute of the specimen based on the first count being larger than the second count.

5. The method of claim 4, wherein generating, for each tile of the set of tiles, the tile-level prediction pertaining to the biological attribute of the tile comprises:

generating, for each tile, a probability of the tile having a candidate biological attribute for each of a set of candidate biological attributes; and selecting the candidate biological attribute from the set of candidate biological attributes having the highest probability;

wherein the confidence level of the tile-level prediction for each tile is based on a difference between a first probability value of the candidate biological attribute selected for the tile and a second probability value of another candidate biological attribute not selected for the tile.

6. The method of claim 3 comprising:

assigning, for each tile of the set of tiles, the tile to a particular cluster of a set of clusters based on the tile-level prediction of the tile, the assignment of a tile to a particular cluster based on a relationship between a tile-level representation and clusters of reference tile-level representations;

determining a distribution of the cluster assignments across the set of clusters based on the tile assignments;

generating the prediction pertaining to the biological attribute of the medical image based on the distribution;

generating a slide-level representation of the medical image based on the distribution; and generating the prediction pertaining to a biological attribute of the specimen based on the slide-level representation.

7. The method of claim 6, wherein the particular cluster is represented by a centroid of the reference tile-level representations and a radius of the cluster; and wherein the assignment of the tile is based on a distance between the tile-level representation and the centroid is within the radius.

8. The method of claim 6, wherein the slide-level representation comprises a multi-dimensional vector of multiple dimensions;

wherein each dimension of the multi-dimensional vector is associated with a cluster of the clusters of reference tile-level representations; and wherein a value of the dimension is based on a count of the tiles assigned to the cluster associated with the dimension.

9. The method of claim 8, wherein the value of the dimension is based on a ratio between the count of the tiles of the set of tiles being in the cluster and a total count of the tiles in the set of tiles.

10. The method of claim 8 wherein:

the medical image is a first medical image of the specimen slide at a first magnification;

the multi-dimensional vector is a first multi-dimensional vector generated from tiles of the first medical image;

the set of clusters is a first set of clusters associated with the first magnification; and the slide-level representation further comprises a second multi-dimensional vector generated based on comparing tile-level representations of tiles of a second medical image of the specimen slide at a second magnification with reference tile-level representations of a second set of clusters associated with a second magnification.

11. The method of claim 10, wherein the tile-level representations and the reference tile-level representations are generated using a machine learning model that maps pixels of a tile to a latent space having a reduced dimension compared with a number of pixels in a tile; and wherein the tile-level representations and the reference tile-level representations comprise embedding vectors.

12. The method of claim 6, wherein the prediction is generated based on inputting the slide-level representation to a machine learning model comprising one or more decision trees, the one or more decision trees being trained using gradient boosting techniques.

13. The method of claim 6, wherein the reference tile representations are associated with reference medical images of other subjects and different biological attributes of the same biological attribute type within the medical data of the other subjects; and wherein the method further comprises:

performing, using the slide-level representation, a similarity search for one or more of the reference medical images that are similar to the medical image, wherein the tile-level prediction pertaining to the biological attribute of the tile is based on the similarity search.

14. The method of claim 13, wherein the same biological attribute type is based on at least one of: a history of treatments of the other subjects, or results of diagnosis of the other subjects.

15. The method of claim 1, wherein the prediction comprises a prediction of a diagnosis of the subject.

16. The method of claim 15, wherein the prediction of the diagnosis of the subject comprises at least one of: a type of tumor of the subject, or a severity of the tumor of the subject.

17. A system for verifying the consistency of electronic medical records, the system comprising:

a database configured to store medical records comprising multi-modal medical data of a plurality of patients, the multi-modal medical data comprising a medical image associated with each of the plurality of patients; and one or more processors programmed and configured to:

access the electronic multi-modal medical data records of a patient of the plurality of patients;

based on a respective medical image, generate a prediction pertaining to a biological attribute of the patient;

determine a degree of consistency between the predicted biological attribute of the patient and other modalities of the multi-modal medical data for the patient; and output, based on the degree of consistency, an indication of whether the electronic multi-modal medical data records for the patient contain inconsistency.

18. The system of claim 17, wherein the one or more processors are programmed and configured to:

based on the respective medical image, generate a plurality of predictions pertaining to a plurality of biological attributes of the patient; and select the biological attribute among the plurality of biological attributes for determining the degree of consistency, the selection based on determining the relevancy of the selected biological attribute to the other multi-modal medical data of the patient.

19. The system of claim 17, wherein the one or more processors are programmed and configured to:

input the respective medical image associated with the patient into a machine learning model, the machine learning model trained to compare the respective medical image with reference medical images of other patients associated with particular biological attributes to predict the biological attribute of the patient; and based on the comparison, determine the degree of consistency between the predicted biological attribute of the patient and other modalities of the multi-modal medical data for the patient.

20. The system of claim 17, wherein the one or more processors are programmed and configured to:

define a set of tiles, wherein each of the set of tiles includes a different portion of the medical image; and generate, for each tile of the set of tiles, a tile-level prediction pertaining to the biological attribute of the tile, wherein the prediction pertaining to the biological attribute of the specimen is generated based on aggregating the tile-level predictions of the set of tiles.

* * * * *